United States Patent [19]

Iwaya et al.

[11] Patent Number: 5,716,542

[45] Date of Patent: Feb. 10, 1998

[54] LIQUID CRYSTAL COMPOUND AND LIQUID CRYSTAL COMPOSITION CONTAINING THE SAME

[75] Inventors: Yukiharu Iwaya; Mamoru Yamada; Hitoshi Kondo; Toshimitsu Hagiwara, all of Kanagawa, Japan

[73] Assignee: Takasago International Corporation, Tokyo, Japan

[21] Appl. No.: 637,284

[22] Filed: Apr. 24, 1996

[30] Foreign Application Priority Data

Apr. 24, 1995 [JP] Japan .................... 7-120464

[51] Int. Cl.$^6$ .................... C09K 19/34; C09K 19/30; C07D 239/02; C07D 213/24
[52] U.S. Cl. .................... 252/299.61; 252/299.63; 544/239; 544/242; 544/298; 544/335; 544/336; 546/342; 546/346
[58] Field of Search .................... 252/299.61, 299.63, 252/299.01; 544/239, 242, 298, 335, 336; 546/342, 346

[56] References Cited

FOREIGN PATENT DOCUMENTS

| 0313338 | 4/1989 | European Pat. Off. . |
| 4-29975 | 4/1992 | Japan . |

*Primary Examiner*—Shean C. Wu
*Attorney, Agent, or Firm*—Sughrue, Mion, Zinn, Macpeak & Seas, PLLC

[57] ABSTRACT

A liquid crystal compound represented by formula (I) and a liquid crystal composition containing the same. The compound exhibits an antiferroelectric liquid crystal phase and has good compatibility with known liquid crystal compounds.

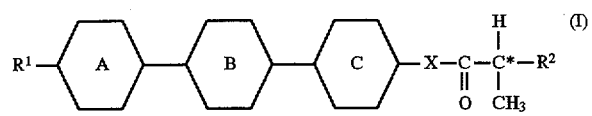

wherein $R^1$ represents a straight-chain or branched alkyl, alkoxy, alkoxycarbonyl, alkanoyloxy or alkoxycarbonyloxy group having 4 to 16 carbon atoms; $R^2$ represents a straight-chain alkyl group having 4 to 10 carbon atoms or a branched alkyl group containing 1 to 3 carbon atoms in its branch and 4 to 12 carbon atoms in total; X represents an oxygen or sulfur atom; rings A and B each represent an F-substituted or unsubstituted phenylene group, a cyclohexylene group or a divalent nitrogen-containing heterocyclic group, provided that either one of rings A and B is the nitrogen-containing heterocyclic group; ring C represents an F-substituted or unsubstituted phenylene group; and C* represents an asymmetric carbon atom.

10 Claims, 1 Drawing Sheet

MHPDBC

LIQUID CRYSTAL COMPOUND AND LIQUID CRYSTAL COMPOSITION CONTAINING THE SAME

FIELD OF THE INVENTION

This invention relates to a novel optically active carboxylic acid ester compound useful as a liquid crystal material for liquid crystal electrooptical devices and to a liquid crystal composition containing the same.

BACKGROUND OF THE INVENTION

Liquid crystal displays have been used in various display embodiments such as watches and desk calculators because of their flatness, lightness, and low electric power consumption. A display system called a twisted nematic system using nematic liquid crystals is adopted in the currently widespread liquid crystal displays. From the standpoint of productivity and cost, the most suitable driving system of liquid crystal displays is simple matrix driving using only electrodes formed on the upper and lower substrates. However, nematic liquid crystals which have been used have a slow response time and undergo a reduction in display contrast as the display density (number of pixels) increases, which has made it difficult to fabricate a high density display using the nematic liquid crystals. To solve this problem, a very expensive driving system called active matrix driving in which each pixel is provided with a thin film transistor (TFT) has been used for displays of computers, etc. Production of displays according to the active matrix driving system involves a great number of steps and therefore entails high cost. Although many efforts have been made for cost reduction, limits have been encountered.

Meyer, et al. reported in 1975 that 4-(n-decyloxybenzylideneamino)cinnamic acid 2-methylbutyl ester they synthesized exhibits a ferroelectric liquid crystal phase (refer to R. B. Meyer, et al., *J. Phys. (France)*, 36, L69 (1975)). Following this report, N. A. Clark, et al. proposed surface-stabilized ferroelectric liquid crystal devices (SSFLD) (refer to N. A. Clark, et al., *Appl. Phys. Lett.*, Col. 36, p. 899 (1980)). It has been expected ever since that a ferroelectric liquid crystal material would make it feasible to produce a liquid crystal display having excellent response properties and bistability, and a large number of ferroelectric liquid crystal materials have been synthesized and proposed to date.

However, a ferroelectric liquid crystal display has not yet been put to practical use since the molecular orientation of ferroelectric liquid crystals proved more complicated than expected in the early stage of studies. That is, the director of liquid crystal molecules is apt to be twisted in layers, under which condition a high contrast cannot be obtained. Further, the layers had been believed to be aligned upright and perpendicular to the upper and lower substrates (bookshelf structure) but, in fact, were found to have a bent structure (chevron structure). As a result, zigzag defects appear, which also cause a reduction in contrast. In addition, it has turned out that the spontaneous polarization occurring in ferroelectric liquid crystal materials gives rise to problems. That is, if a memory state is maintained for a long period of time, inversion becomes difficult even on application of an opposite electrical field (this phenomenon will hereinafter be referred to as ghost effect), which eventually causes a reduction in contrast.

In recent years, existence of a liquid crystal phase that might eliminate the above-described disadvantages of ferroelectric liquid crystals has been reported. This liquid crystal phase is an antiferroelectric liquid crystal phase (hereinafter referred to as an ScA* phase) which has a third stable state as well as the two stable states (bistable state) possessed by a ferroelectric liquid crystal phase. In the third state the molecular tilt direction is reversed between adjacent layers to offset spontaneous polarization. While the ScA* phase appears on the lower temperature side of an Sc* phase, it has substantially the equal switching time to the Sc* phase's. The layer structure can be switched, alternating between a chevron structure and a bookshelf structure. Therefore in the ScA* phase a bookshelf structure can easily be obtained on application of an electrical field, thereby eliminating the zigzag defects. Further, since a polarizer and an analyzer can be arranged taking the third state, which is a stable state with no voltage applied, as a dark state, and the two ferroelectric states can alternate with each other on application of an alternating electrical field, ghost effect observed with ferroelectric liquid crystal devices does not occur.

As stated above, an antiferroelectric liquid crystal device can be driven by an inexpensive and highly productive simple matrix driving system and is said to realize high contrast displaying with ease. An antiferroelectric liquid crystal phase of smectic I phase origin having a higher order (SIA* phase) is also known as an antiferroelectric liquid crystal phase. However, because the SIA* phase is a phase of higher order, a fast switching time cannot be obtained. Thus, the present invention will be explained with reference to an ScA* phase which can assure a fast response time.

The following compound (hereinafter referred to as MHPOBC) is the first to be found to exhibit an antiferroelectric liquid crystal phase (see Chandani, et al., *Jpn. J. Appl. Phys.*, Vol. 27, L729 (1988)).

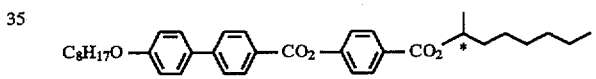

It was then proved that an ScA* phase also appears even with the chiral site of MHPOBC being changed from the 1-methylheptyl group to a 1-trifluoromethylheptyl group. Since the antiferroelectric liquid crystal phase appearing in this compound having a 1-trifluoromethylheptyl group is relatively stable, many of the compounds which have been reported to exhibit an ScA* phase belong to derivatives of this compound.

If the 1-methylheptyl group of MHPOBC is replaced with a 1-methylhexyl group, only a ferroelectric liquid crystal phase appears with no ScA* phase observed. If it is replaced with a 2-methylalkyl group, an ScA* phase is not at all observed. It is thus difficult to structurally modify the chiral site, and molecular modification of the chiral site has scarcely been attempted. Hence, it has been a general tendency to synthesize various compounds by introducing modifications chiefly to the liquid crystal core, especially the cyclic structure. Because various properties are required in order for antiferroelectric liquid crystal materials to be put to practical use similarly to the conventional nematic liquid crystals, it is difficult to satisfy the performance requirements simply by using only a single group of compounds or only the above-mentioned analogous compounds, and compounding of a number of compounds having different properties is necessary.

On the other hand, the inventors of the present invention previously found that an antiferroelectric liquid crystal phase appears in the compound shown below as disclosed in JP-A-4-82862 (the term "JP-A" as used herein means an "unexamined published Japanese patent application").

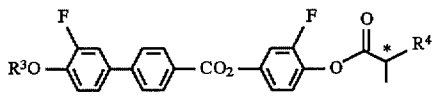

Although the above compound containing a 2-methylalkanoic ester group exhibits an antiferroelectric liquid crystal phase stably, it has high viscosity owing to its biphenylcarboxylic acid phenyl ester core structure common to MHPOBC. Because of the structural similarity between this compound and MHPOBC, much improvement in characteristics as well as viscosity cannot be expected of this compound.

2-(4-Hexyloxyphenyl)-5(4-(1-methylpentylcarbonyloxy) phenyl)pyrimidine represented by the following formula, another compound having introduced therein a 2-methylalkanoic acid, is disclosed in JP-A-4-29975.

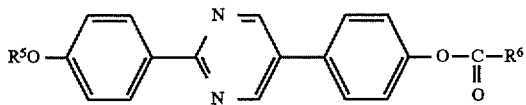

wherein $R^5$ and $R^6$ each represent an alkyl group having 1 to 18 carbon atoms, which may have a branch.

The compounds of JP-A-4-29975 differ from the liquid crystal compounds of the present invention in the direction the pyrimidine ring faces, and none of them exhibits an antiferroelectric phase.

The compounds disclosed in JP-A-63-170367, which are represented by the formula shown below, can be mentioned as compounds relevant to the present invention.

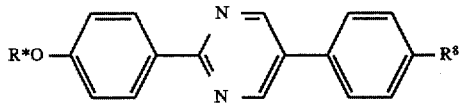

wherein $R^8$ represents an alkyl or alkoxy group; and $R^*$ represents an optically active alkyl or acyl group having an asymmetric carbon atom in the chain thereof.

These compounds, 2-phenyl-5-phenylpyrimidine derivatives, seemingly embrace part of the 2-methylalkanoic acid derivatives represented by formula (I) according to the present invention. More specifically, there is only one compound disclosed in JP-A-63-170367 that is included in formula (I), provided that $R^2$ is n-$C_2H_5$. The publication clearly states that this compound exhibits a series of phases, SA-Sc*-Sx, disclosing existence of an unidentified smectic phase (Sx) on the lower temperature side of the Sc* phase. In an attempt to identify the unidentified smectic phase of this compound, the inventors of the present invention synthesized the compound as shown in Comparative Examples hereinafter described. As a result, it has been revealed that the phase is obviously of a smectic B phase origin of higher order and is not an antiferroelectric liquid crystal phase as described in Comparative Examples 3 to 5.

JP-A-3-12478 discloses compounds for use in liquid crystal compositions showing a ferroelectric chiral smectic C phase. Of the compounds disclosed, the compound having the following formula is the only one that is included in formula (I), provided that $R^2$ is n-$C_2H_5$.

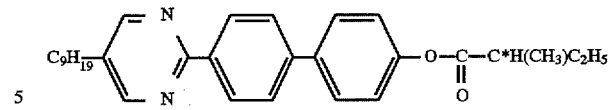

The publication has no mention of the phase transition temperature of the above compound. The inventors of the present invention synthesized the compound and studied its phase transition. As a result, no antiferroelectric liquid crystal phase was exhibited as described in Comparative Example 6.

Therefore, one cannot predict from the compound of JP-A-3-12478 that any compound represented by formula (I) may exhibit an antiferroelectric liquid crystal phase.

SUMMARY OF THE INVENTION

Seeking for liquid crystal compounds which have low viscosity and exhibit an antiferroelectric liquid crystal phase, the inventors have synthesized a large number of compounds assuming an antiferroelectric liquid crystal phase by optimizing the facing direction of a nitrogen-containing heterocyclic ring and the length of an alkyl group bonded to an asymmetric carbon atom. The present invention has been completed based on this finding.

An object of the present invention is to provide a novel liquid crystal compound exhibiting an antiferroelectric liquid crystal phase and having satisfactory miscibility with known antiferroelectric liquid crystal compounds and a liquid crystal composition containing the same.

As a result of extensive research into compounds showing an antiferroelectric liquid crystal phase, the inventors reached the present invention. That is, the present invention provides in its first aspect a liquid crystal compound represented by the formula:

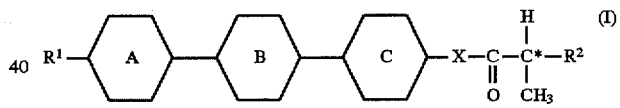

wherein $R^1$ represents a straight-chain or branched alkyl, alkoxy, alkoxycarbonyl, alkanoyloxy or alkoxycarbonyloxy group having 4 to 16 carbon atoms; $R^2$ represents a straight-chain alkyl group having 4 to 10 carbon atoms or a branched alkyl group containing 1 to 3 carbon atoms in its branch and 4 to 12 carbon atoms in total; X represents an oxygen or sulfur atom;

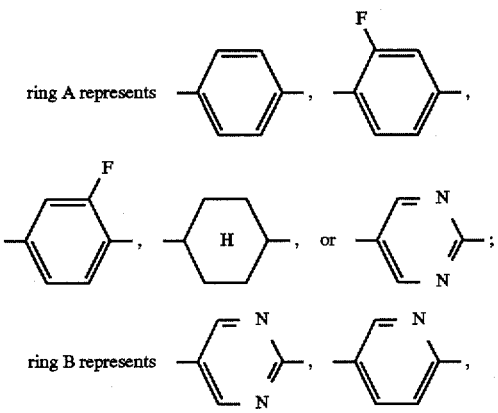

-continued

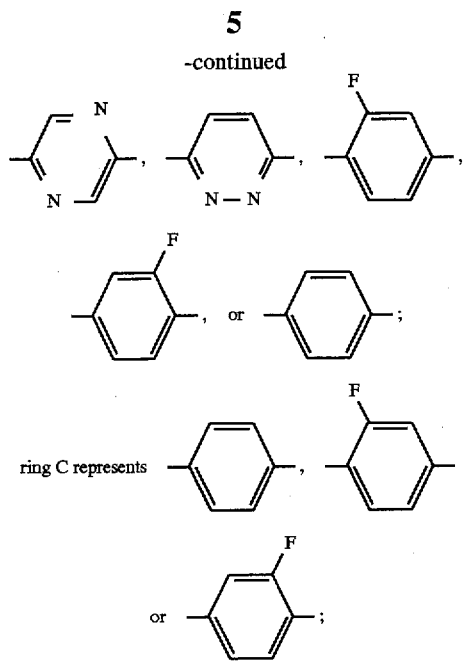

either ring A or ring B represents the above-mentioned nitrogen-containing heterocyclic ring; and C* represents an asymmetric carbon atom.

The invention also provides in its second aspect a liquid crystal composition containing at least one liquid crystal compound represented by formula (I).

DETAILED DESCRIPTION OF THE INVENTION

Figure 1:
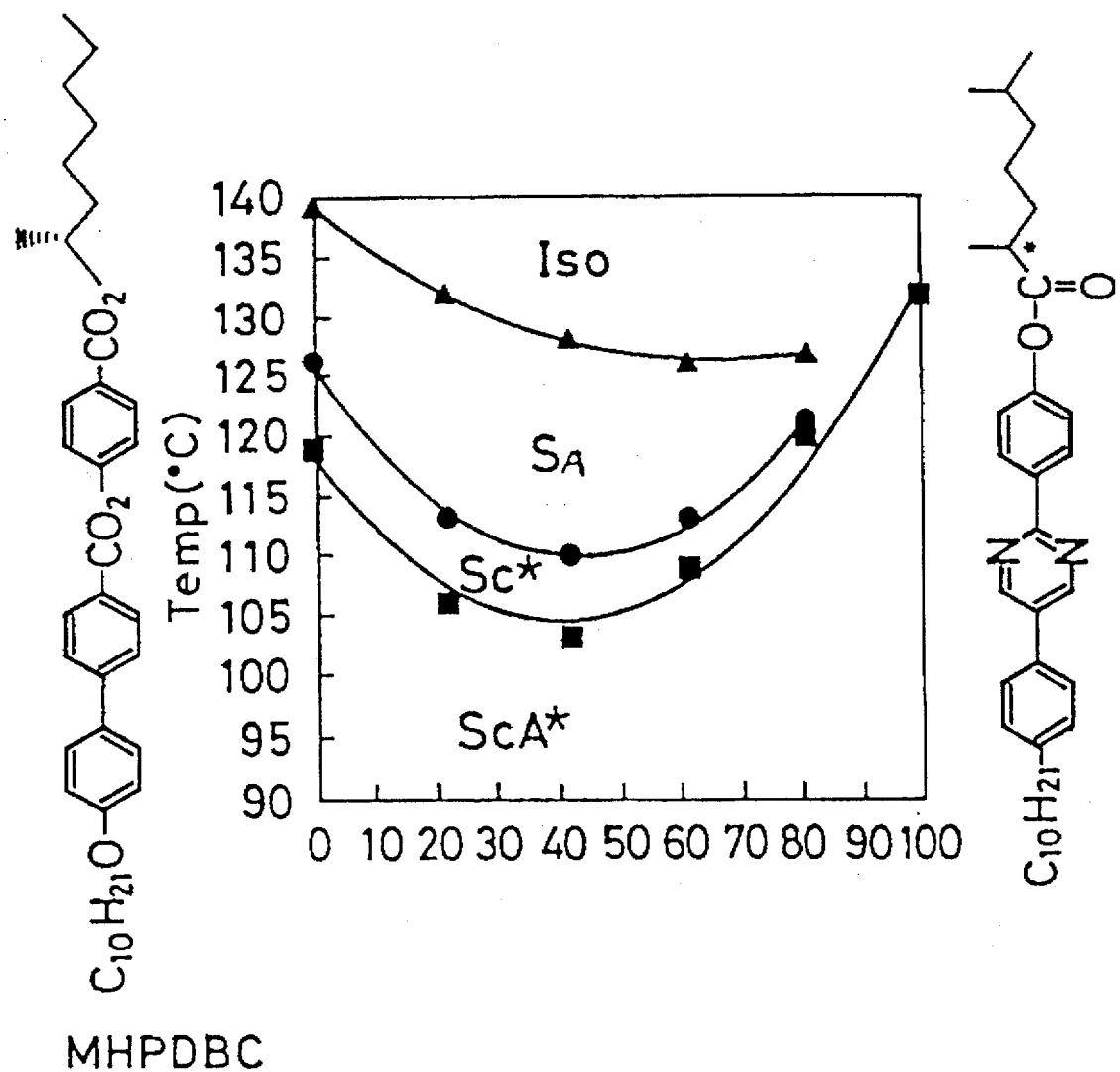
FIG. 1 is a phase diagram of the compound of Example 1 and a known compound (MHPDBC).

In formula (I), the alkyl group, alkoxy group, alkoxycarbonyl group, alkanoyloxy group and alkoxycarbonyloxy group as $R^1$ may be either straight or branched. Straight-chain groups are preferred. Those containing 6 to 12 carbon atoms are still more preferred. The alkyl group as $R^2$ may be either a straight-chain group having 4 or more carbon atoms or a branched group having a straight chain moiety containing 3 or more carbon atoms and having 4 or more carbon atoms in total. Of the compounds having no fluorine atom in the core thereof, those in which $R^2$ contains 4 to 6 carbon atoms in the straight-chain moiety thereof are preferred for their viscosity and stability in exhibiting an antiferroelectric liquid crystal phase. Of the compounds having a fluorine atom in the core, those in which $R^2$ contains 3 to 8 carbon atoms in the straight-chain moiety thereof are preferred. In addition, the compounds in which ring A or B is a pyridine ring or a pyrimidine ring are particularly preferred.

Preferred examples of the compounds of formula (I) are shown below.

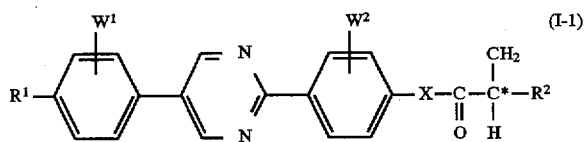

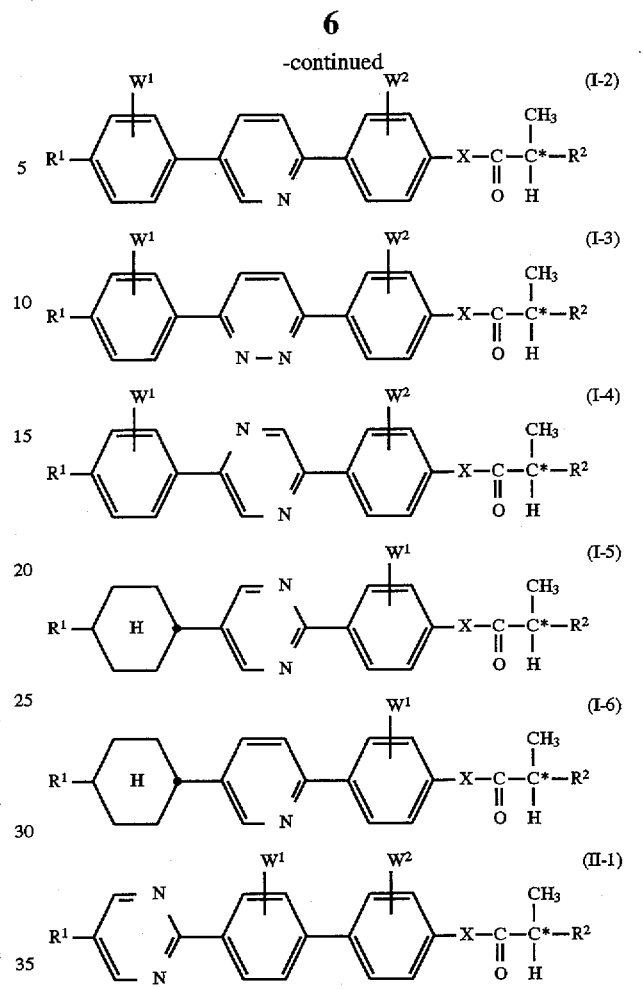

wherein $W^1$ and $W^2$ each represent a hydrogen atom or a fluorine atom; and X, $R^1$, and $R^2$ are as defined above.

While the compounds of the invention exhibit antiferroelectric properties when used alone, two or more of them can be compounded into an antiferroelectric liquid crystal composition. Further, the compounds of the invention have good miscibility with known antiferroelectric liquid crystal compounds, and they can also be combined with the known antiferroelectric liquid crystal compounds to easily afford antiferroelectric liquid crystal compositions. Preferred antiferroelectric liquid crystal compounds with which the compounds of the invention can preferably be combined include those having the following end groups.

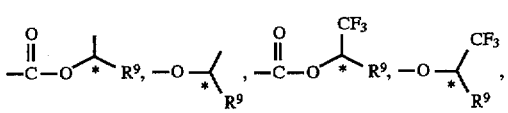

wherein $R^9$ represents a straight-chain alkyl group.

Specific examples which can preferably used in combination with the compounds of the invention are shown below.

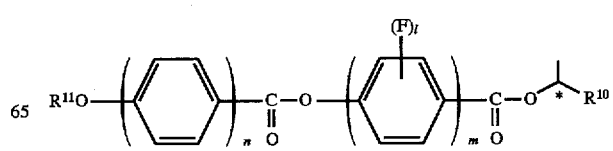

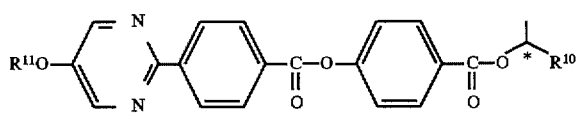

wherein $R^{10}$, $R^{11}$ each represent a straight-chain alkyl group; m and n each represent 1 or 2 giving the sum (m+n) of 3; and l represents 0 or 1.

Where the liquid crystal compounds of the invention are mixed with the above-described known antiferroelectric liquid crystal compounds or compositions thereof, the liquid crystal compounds of the invention are preferably used in a proportion of 1 to 80% by weight, still preferably 1 to 40% by weight, based on the total composition.

The liquid crystal compounds of the invention exhibit high miscibility also with those known compounds which show a smectic C or chiral smectic C phase and exhibit no antiferroelectric liquid crystal phase, such as phenylpyridine compounds and phenylbenzoate compounds. Therefore, the compounds of the invention can be mixed with such compounds to provide antiferroelectric liquid crystal compositions as long as the layer structure of the antiferroelectric liquid crystal phase can be retained. In this case, the liquid crystal compound of the invention and the aforesaid known antiferroelectric liquid crystal compound or a composition thereof are preferably used in a total proportion of 60 to 99% by weight, still preferably 60 to 80% by weight, based on the total composition.

Thus, many of the liquid crystal compounds of the invention exhibit a very stable antiferroelectric liquid crystal phase and can be used in electrooptical devices using antiferroelectric liquid crystals. The compounds of the invention have good miscibility with many other conventional liquid crystal compounds and can therefore be combined with them to provide liquid crystal materials with improved temperature characteristics.

The liquid crystal compounds of formula (I) of the invention can be synthesized by, for example, preparing an optically active 2-substituted alkanoic acid by asymmetric hydrogenation of a corresponding 2-substituted-2-alkenoic acid or optical resolution of a racemic 2-substituted alkanoic acid or a derivative thereof using lipase and then reacting the optically active 2-substituted alkanoic acid with a phenol or thiophenol derivative represented by the formula:

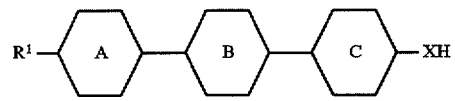

wherein X represents an oxygen or sulfur atom, and $R^1$, A, B and C are as defined above, which is synthesized in a conventional manner.

Reaction schemes for synthesizing the phenol or thiophenol derivative and the compounds of formula (I) are illustrated below.

(1) Ring B = pyrimidine ring:

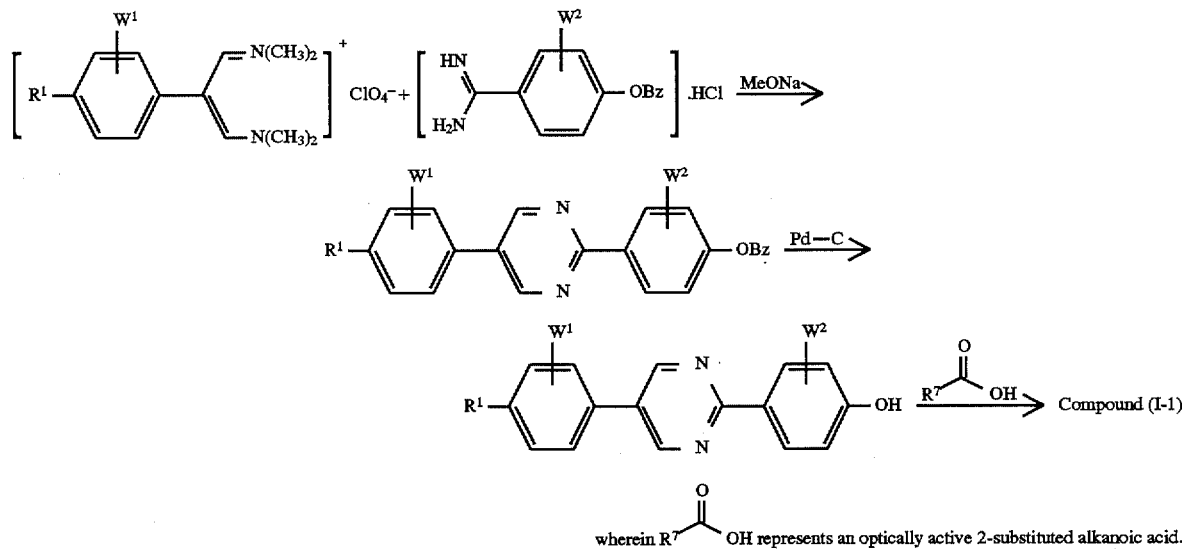

wherein $R^7 \overset{O}{\underset{}{\text{C}}} OH$ represents an optically active 2-substituted alkanoic acid.

(2) Ring B = pyridine ring:

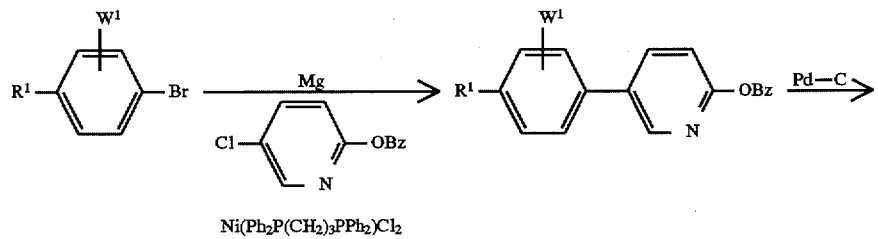

-continued
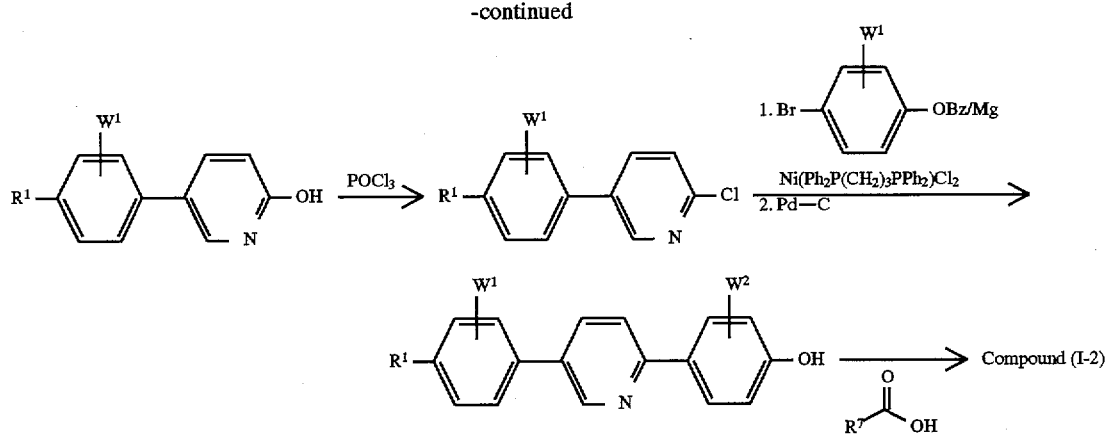
(3) Ring A = pyrimidine ring:
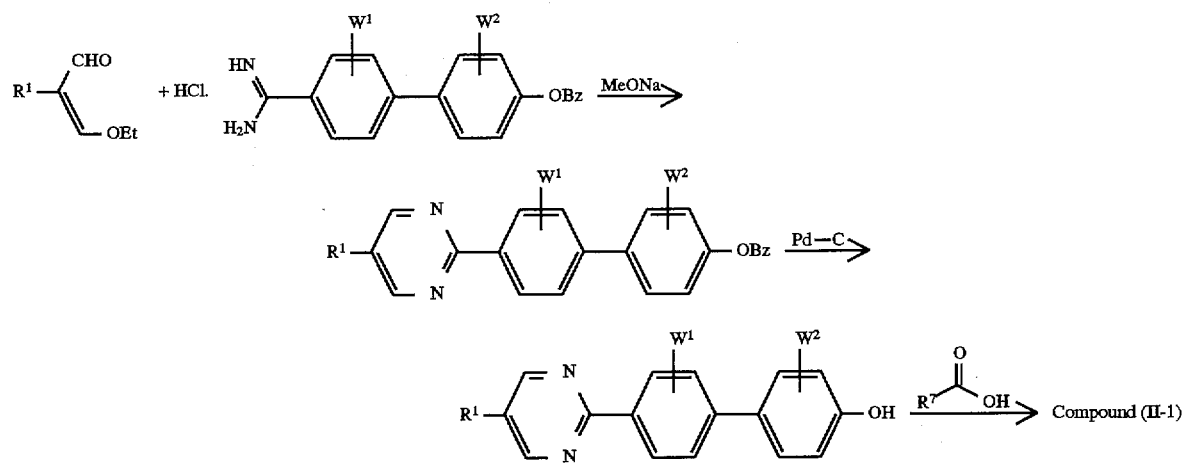
(4) Ring B = pyridazine ring:
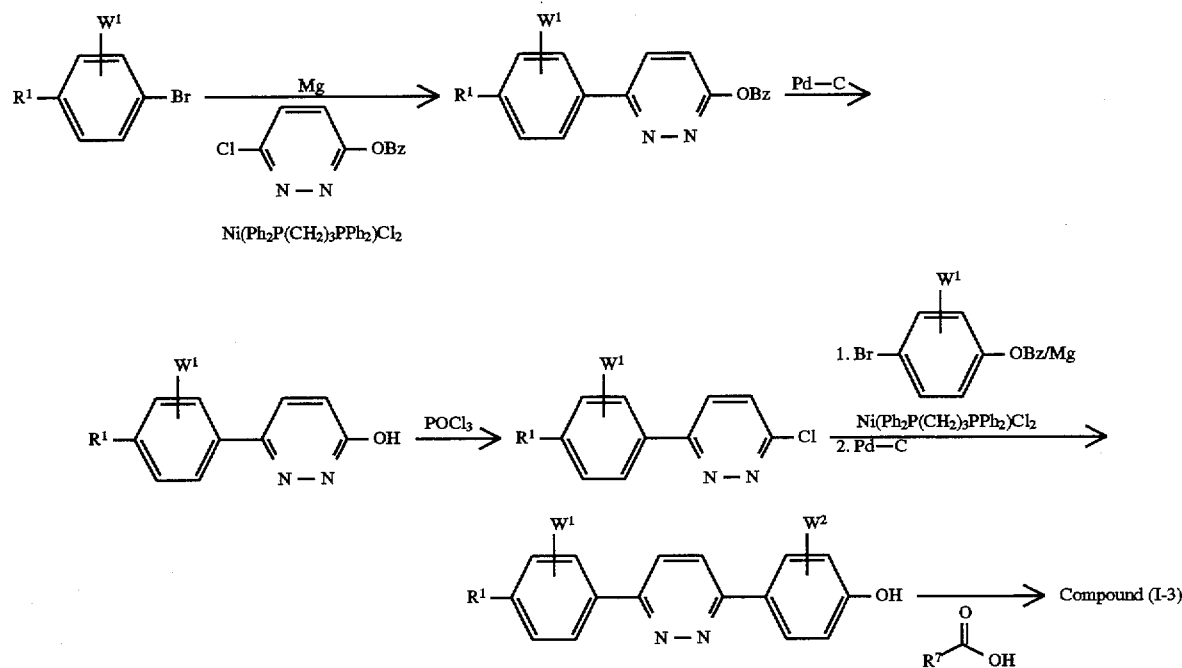

(5) Ring B = pyrazine ring:

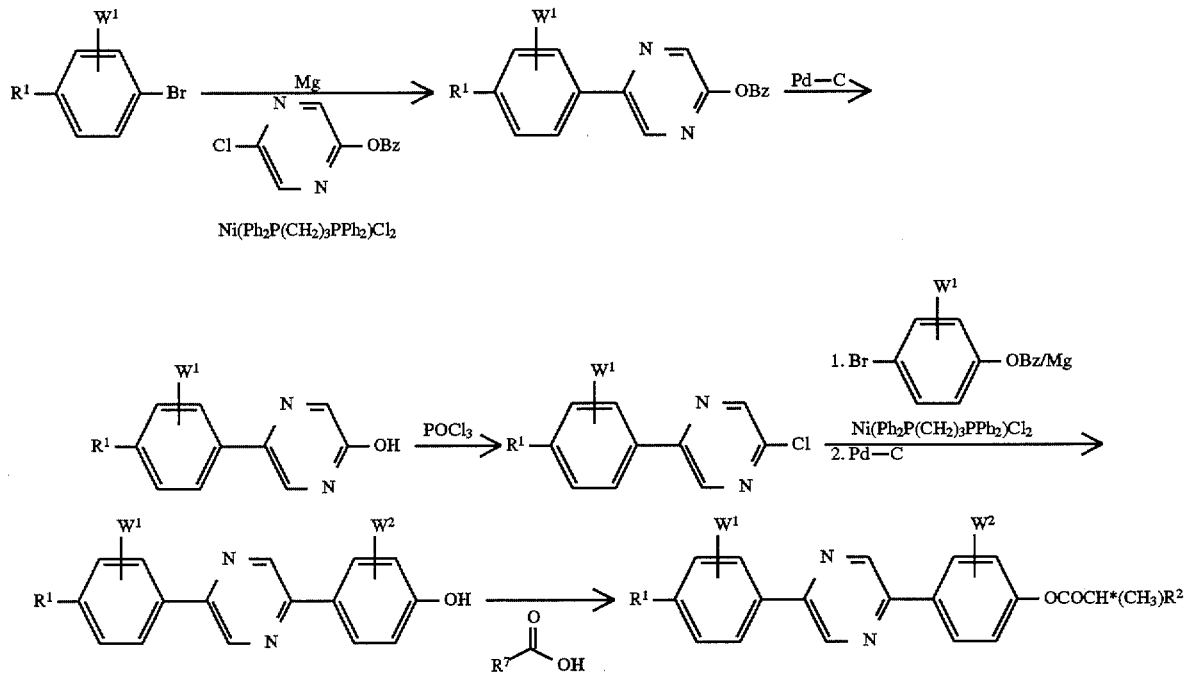

Thiophenol intermediates can be obtained from the phenol intermediates prepared by the above-described processes (1) to (5) in accordance with the following reaction scheme in which the phenol derivative is reacted to obtain an O-aryldialkylthiocarbamate, which is then rearranged into an S-aryldialkylthiocarbamate by heating, followed by hydrolysis.

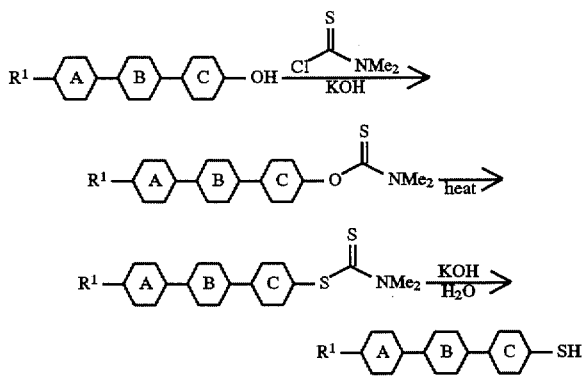

The present invention will now be illustrated in greater detail with reference to Examples, but it should be understood that the present invention is not limited thereto. Unless otherwise indicated, all the percents are by weight. The phase transition temperatures of the liquid crystal compounds prepared were decided by observation under a polarizing microscope and differential scanning calorimetry (DSC). Identification of the antiferroelectric liquid crystal phase of a compound or a mixture of compounds was conducted by a so-called miscibility test.

EXAMPLE 1

Synthesis of 2-(4-((S)-2,6-Dimethylheptanoyloxy) phenyl-5-4-decylphenyl-1,3-pyrimidine 1) Synthesis of 5-(4-Decylphenyl)-2-(4-benzyloxyphenyl)-1,3-pyrimidine (Intermediate 1-1):

In a 200 ml three-necked flask were charged 5.55 g (12.6 mmol) of {3-dimethylamino-2-(4-decylphenyl) propenylidene}dimethylammonium perchlorate, 3.0 g (11.4 mmol) of 4-benzyloxybenzamidine hydrochloride, and 130 ml of ethanol in a nitrogen stream, and 6.6 g of a 28% methanol solution of sodium methoxide was added thereto dropwise with 20 ml of ethanol under cooling with ice. After the addition, the mixture was allowed to react at an ethanol refluxing temperature for 22 hours. After completion of the reaction, the reaction mixture was poured into 300 ml of water, followed by filtration. The precipitated crystals as collected on the filter paper were washed with methanol and dried to give 4.22 g of the title compound in a yield of 92%.

2) Synthesis of 5-(4-Decylphenyl)-2-(4-hydroxyphenyl)-1, 3-pyrimidine (Intermediate 1-2):

In a 300 ml four-necked flask were charged 4.20 g (10.4 mmol) of intermediate 1-1, 40 ml of methanol, and 80 ml of tetrahydrofuran (hereinafter abbreviated as THF). To the mixture was added 0.84 g of palladium-carbon to conduct hydrogenation at 40° C. for 3 hours. After completion of the reaction, palladium-carbon was separated by filtration, and the filtrate was purified by column chromatography on silica gel (hereinafter simply expressed as column chromatography) using 50 g of silica gel and a 10:1 (by volume) mixture of toluene:ethyl acetate as a developing solvent to give 3.15 g of the title compound in a yield of 97%.

3) Synthesis of 2-(4-((S)-2,6-Dimethylheptanoyloxy) phenyl)-5-(4-decylphenyl)-1,3-pyrimidine:

In a 200 ml four-necked flask were charged 1.00 g (3.2 mmol) of intermediate 1-2, 0.45 g (3.2 mmol) of (S)-2,6-dimethylheptanoic acid, 0.867 g (4.2 mmol) of N,N'-dicyclohexylcarbodiimide (hereinafter abbreviated as DCC), and 50 ml of dichloromethane in a nitrogen stream, and 0.04 g (0.32 mmol) of 4-dimethylaminopyridine was added thereto, followed by allowing the mixture to react at room temperature for 3.5 hours. After completion of the reaction, the reaction mixture was filtered and purified by column chromatography using 50 g of silica gel and a 10:1

(by volume) mixture of toluene and ethyl acetate as a developing solvent to give 1.25 g of crude crystals. Recrystallization from 40 ml of ethanol and 5 ml of chloroform and fractionation on an ODS column (acetonitrile:methanol:chloroform=85:10:5 by volume) yielded 0.82 g of the title compound (yield: 59%).

$^1$H-NMR (CDCl$_3$) δ ppm: 0.89 (9H, m), 1.26 (12H, m), 1.33 (6H, m), 1.35 (1H, m), 1.44 (2H, m), 1.66 (2H, m), 1.82 (1H, m), 2.69 (3H, m), 7.22 (2H, d, J=8.8 Hz), 7.34 (2H, d), 7.54 (2H, d), 8.52 (2H, d, J=8.8 Hz), 8.99 (2H, s)

MS (m/e): 528 (M$^+$)

The resulting compound melted at 100.7° C., at which it exhibited an antiferroelectric liquid crystal phase, and changed to an isotropic phase at 131.7° C. In FIG. 1 is shown a phase diagram of the resulting compound and MHPDBC (4"-(1-Methylheptyl)oxycarbonylphenyl-4-decyloxybiphenyl-4'-carboxylate), a known compound exhibiting an antiferroelectric liquid crystal phase. As can be seen from the diagram, although the thermal stability of the whole liquid crystal phase tends to be reduced upon mixing, the liquid crystal phase observed in the compound of Example 1 is miscible with the antiferroelectric liquid crystal phase of the standard substance, thus proving to have the same liquid crystal phase as the standard substance.

EXAMPLE 2

Synthesis of 2-{4-((S)-2,6-Dimethylheptanoyloxy)phenyl}-5-(4-decyloxyphenyl)-1,3-pyrimidine The title compound was synthesized in the same manner as in Example 1, except for replacing the {3-dimethylamino-2-(4-decylphenyl)propenylidene}dimethylammonium perchlorate used in Example 1-(1) with 3-dimethylamino-2-(4-decyloxyphenyl)propenylidene}dimethylammonium perchlorate.

$^1$H-NMR (CDCl$_3$) δ ppm: 0.89 (9H, m), 1.23 (12H, m), 1.26 (6H, m), 1.35 (1H, m), 1.44 (6H, m), 1.82 (1H, m), 2.72 (1H, m), 2.82 (2H, t), 7.04 (2H, d, J=8.9 Hz), 7.21 (2H, d, J=8.8 Hz), 7.55 (2H, d, J=8.9 Hz), 8.50 (2H, d, J=8.8 Hz), 8.96 (2H, s)

MS (m/e): 544 (M$^+$)

The compound melted at 89.3° C., at which it exhibited an antiferroelectric liquid crystal phase, and changed to an isotropic phase at 149° C.

EXAMPLE 3

Synthesis of 2-(4-((S)-2-Methylhexanoyloxy)phenyl)-5-(4-decylphenyl)-1,3-pyrimidine The title compound was synthesized in the same manner as in Example 1, except for replacing the (S)-2,6-dimethylheptanoic acid used in Example 1-(3) with (S)-2-methylhexanoic acid.

$^1$H-NMR (CDCl$_3$) δ ppm: 0.88 (3H, t), 0.95 (3H, t), 1.35 (21H, m), 1.65 (3H, m), 1.85 (1H, m), 2.68 (2H, m), 7.22 (2H, d, J=8.9 Hz), 7.34 (2H, d, J=8.3 Hz), 7.54 (2H, d, J=8.3 Hz), 8.52 (2H, d, J=8.9 Hz), 9.00 (2H, s)

MS (m/e): 500 (M$^+$)

The compound melted at 91.3° C., at which it exhibited an antiferroelectric liquid crystal phase, and changed to a ferroelectric liquid crystal phase (Sc* phase) at 130° C., a smectic A phase at 139° C., and then an isotropic phase at 143.5° C.

EXAMPLE 4

Synthesis of 2-(4-((S)-2,6-Dimethylheptanoyloxy)-3-fluorophenyl)-5-(4-octylphenyl)-1,3-pyrimidine The title compound was synthesized in the same manner as in Example 1, except for replacing the {3-dimethylamino-2-(4-decylphenyl)propenylidene}dimethylammonium perchlorate with 3-dimethylamino-2-(4-octylphenyl)propenylidene}dimethylammonium perchlorate and replacing the 4-benzyloxybenzamidine hydrochloride with 4-benzyloxy-3-fluorobenzamidine hydrochloride in Example 1-(1).

$^1$H-NMR (CDCl$_3$) δ ppm: 0.90 (9H, m), 1.28 (16H, m), 1.34 (2H, m), 1.66 (3H, m), 1.83 (1H, m), 2.68 (2H, m), 2.77 (1H, m), 7.23 (2H, d, J=9.0 Hz), 7.34 (2H, d, J=8.3 Hz), 7.55 (2H, d, J=8.3 Hz), 8.31 (2H, d, J=9.0 Hz), 8.99 (2H, s)

MS (m/e): 518 (M$^+$)

The compound melted at 97.3° C., at which it exhibited an antiferroelectric liquid crystal phase, and changed to an isotropic phase at 125.8° C.

EXAMPLE 5

Synthesis of 2-(4-((S)-2,6-Dimethylheptanoyloxy)phenyl)-5-(3-fluoro-4-decyloxyphenyl)-1,3-pyrimidine The title compound was synthesized in the same manner as in Example 1, except for replacing the {3-dimethylamino-2-(4-decylphenyl)propenylidene}dimethylammonium perchlorate used in Example 1-(1) with 3-dimethylamino-2-(4-decyloxy-3-fluorophenyl)propenylidene}dimethylammonium perchlorate.

$^1$H-NMR (CDCl$_3$) δ ppm: 0.89 (9H, m), 1.29 (23H, m), 1.86 (3H, m), 2.72 (1H, m), 4.10 (2H, t), 7.11 (1H, s), 7.22 (2H, d, J=8.9 Hz), 7.35 (2H, d), 8.51 (2H, d, J=8.8 Hz), 8.94 (2H, s)

MS (m/e): 562 (M$^+$)

The compound melted at 105.2° C., at which it exhibited an antiferroelectric liquid crystal phase, and changed to an isotropic phase at 118.6° C.

EXAMPLE 6

Synthesis of 2-{3-Fluoro-4-((S)-2,6-dimethylheptaonyloxy)phenyl}-5-(4-decylphenyl)-pyridine 1) Synthesis of 4-Decylbromobenzene:

In a reaction flask were charged 10.2 g of metallic magnesium, 100 ml of THF, and a small amount of iodine in a nitrogen stream, and a part of 500 ml of a THF solution containing 100 g of 1,4-dibromobenzene was added thereto dropwise to initiate reaction. Then, the rest of the solution was added dropwise at 25° to 30° C. over a 2-hour period, and the mixture was allowed to react at 40° C. for 1 hour, followed by cooling to prepare a Grignard reagent. Separately, 187 g of decyl bromide, 500 ml of benzene, 98.3 g of N,N,N',N'-tetramethylethylenediamine, and 2.1 g of copper (I) chloride were put in a reaction flask, and the atmosphere was displaced with nitrogen. The mixture was heated to 50° C., and the above prepared Grignard reagent was added thereto dropwise at that temperature over 30 minutes. The reaction mixture was allowed to react for 24 hours, cooled, and poured into a saturated aqueous ammonium solution, and extracted with ethyl acetate. The extract was washed with water and dried over magnesium sulfate to recover 107 g of a crude product. The crude product was distilled in a Claisen flask equipped with a Vigreaux tube cylinder to obtain 43.7 g of the title compound.

2) Synthesis of 2-Benzyloxy-5-chloropyridine:

In a reaction flask were charged 10 g of 5-chloro-2-hydroxypyridine, 11.73 g of benzyl chloride, 16 g of potassium carbonate, and 250 ml of dimethylformamide in a nitrogen stream, and the mixture was reacted at 80° C. for 2 hours. After cooling, the organic layer was filtered, and the salt was washed with ethyl acetate and filtered. The solvent was evaporated, and the residue was purified by column chromatography using 150 g of silica gel and a 5:1 (by volume) mixture of toluene and ethyl acetate as a developing solvent to give 14.5 g of the title compound.

3) Synthesis of 2-Benzyloxy-5-(4-decylphenyl)-pyridine:

In a reaction flask were charged 2.17 g of magnesium, 50 ml of THF, and a small amount of iodine in a nitrogen stream. A part of a solution of 26.8 g of 4-decylbromobenzene in 134 ml of THF was added thereto dropwise to initiate reaction. The rest of the solution was added thereto dropwise at 35° to 40° C. over 1 hour, and the mixture was allowed to react at that temperature for 2 hours, followed by cooling to prepare a Grignard reagent. In a reaction flask previously purged with nitrogen were charged 15.2 g of 2-benzyloxy-5-chloropyridine, 150 ml of THF, and 2.68 g of $Ni(Ph_2P(CH_2)_3PPh_2)Cl_2$, and the above prepared Grignard reagent was added thereto dropwise over a 20-minute period. After the addition, the reaction was further continued at the same temperature for 1 hour. The reaction mixture was poured into ice-water and extracted with toluene. The organic layer was separated by filtration, and the solvent was removed therefrom by evaporation to give 37.18 g of a crude product. Purification by column chromatography using 450 g of silica gel and a 5:1 (by volume) mixture of toluene and ethyl acetate gave 19.9 g of the title compound.

4) Synthesis of 5-(4-Decylphenyl)-2-hydroxypyridine:

In a reaction flask were charged 19.9 g of 2-benzyloxy-5-(4-decylphenyl)pyridine and 400 ml of methanol. After purging with nitrogen, 3 g of palladium-carbon was added. After the atmosphere was displaced with hydrogen, the inner temperature was raised up to 66° C. and then dropped to 40° C. The heating and cooling cycle was repeated two more times to complete the reaction. The reaction mixture was cooled and filtered, and the solvent was removed by evaporation to obtain 15.0 g of a crude product. Purification of the crude product by column chromatography using 150 g of silica gel and a 1:1 mixture (by volume) of ethyl acetate and ethanol afforded 12.3 g of the title compound.

5) Synthesis of 2-Chloro-5-(4-decylphenyl)pyridine:

In a reaction flask were charged 12.3 g of 5-(4-decylphenyl)-2-hydroxypyridine and 30.2 g of phosphorus oxychloride, and the mixture was allowed to react at 100° C. for 6 hours. After completion of the reaction, the reaction mixture was cooled, slowly poured into ice-water, and extracted with toluene. The organic layer was washed with water, dried, and evaporated to remove the solvent. The resulting crude product was subjected to column chromatography using 150 g of silica gel and a 3:1 mixture (by volume) of toluene and ethyl acetate as a developing solvent to give 5.55 g of the title compound.

6) Synthesis of 2-(3-Fluoro-4-methoxyphenyl)-5-(4-decylphenyl)pyridine:

In a reaction flask were charged 0.88 g of magnesium, 50 ml of THF, and a small amount of iodine in a nitrogen stream, and a small portion of a solution of 7.27 g of 3-fluoro-4-methoxy-1-bromobenzene in 72 ml of THF was added thereto to initiate reaction. Then, the rest of the solution was added thereto dropwise at 35° to 40° C., and the mixture was reacted at the same temperature for 1 hour to prepare a Grignard reagent. Separately, 5.55 g of 2-chloro-5-(4-decylphenyl)pyridine, 100 ml of THF, and 0.72 g of $Ni(Ph_2P(CH_2)_3PPh_2)Cl_2$ were put to another reaction flask, and the above prepared Grignard reagent was added thereto dropwise over a 20-minute period. After the addition, the reaction was further continued at the same temperature for 1 hour. The reaction mixture was poured into ice-water and extracted with toluene. The solvent was evaporated to give 11.0 g of a crude product. The crude product was purified by column chromatography using 150 g of silica gel and a 5:1 (by volume) mixture of toluene and ethyl acetate to give 7.0 g of crude crystals. The crude crystals were dissolved in a mixed solvent of 20 ml of chloroform and 200 ml of ethanol, cooled to 5° C., and filtered to obtain 5.61 g of the title compound.

7) Synthesis of 2-(3-Fluoro-4-hydroxyphenyl)-5-(4-decylphenyl)pyridine:

In a reaction flask were charged 5.61 g of 2-(3-fluoro-4-methoxyphenyl)-5-(4-decylphenyl)pyridine, 168 ml of acetic acid, and 102 ml of 47% hydrobromic acid, and the mixture was reacted at 110° C. overnight. After cooling, the reaction mixture was poured into ice-water, and the precipitated crystals were collected by filtration, washed with water, dissolved in THF, dehydrated over sodium sulfate, and evaporated to remove THF to yield 6.5 g of the title compound.

8) Synthesis of 2-(3-Fluoro-4-((S)-2,6-dimethylheptanoyloxy)phenyl)-5-(4-decylphenyl)pyridine:

The title compound was obtained in the same manner as in Example 1-(3) except for replacing the 5-(4-decylphenyl)-2-(4-hydroxyphenyl)-1,3-pyrimidine with 2-(3-fluoro-4-hydroxyphenyl)-5-(4-decylphenyl)pyridine. Yield: 20.08%.

$^1$H-NMR (CDCl$_3$) δ ppm: 0.89 (9H, m), 1.29 (23H, m), 1.57 (2H, m), 1.82 (1H, m), 2.67 (2H, m), 2.77 (1H, m), 7.22 (2H, d), 7.31 (2H, d), 7.55 (2H, d), 7.74 (1H, d), 7.76 (1H, d), 7.94 (2H, d), 8.91 (2H, s)

MS (m/e): 545 (M$^+$)

The compound melted at 49.5° C., and changed to an antiferroelectric liquid crystal phase at 72.5° C. via a smectic phase of high order, and then to an isotropic phase at 129.6° C.

EXAMPLE 7

Synthesis of 2-(4-((S)-2,6-Dimethylheptanoyloxy)-2-fluorophenyl)-5-(4-decylphenyl)-1,3-pyrimidine The title compound was synthesized in the same manner as in Example 1 except for replacing the 4-benzyloxybenzamidine hydrochloride used in Example 1-(1) with 4-benzyloxy-2-fluorobenzamidine hydrochloride.

$^1$H-NMR (CDCl$_3$) δ ppm: 0.89 (9H, m), 1.28 (23H, m), 1.86 (3H, m), 1.57 (1H, m), 1.66 (2H, m), 1.80 (1H, m), 2.69 (3H, m), 7.04 (2H, m), 7.34 (2H, d, J=8.4 Hz), 7.55 (2H, d, J=8.3 Hz), 8.20 (1H, m), 9.05 (2H, s)

MS (m/e): 406 (M$^+$)

The compound melted at 77.8° C., at which it exhibited an antiferroelectric liquid crystal phase, and changed to an isotropic phase at 94.2° C.

EXAMPLE 8

Synthesis of 2-(4-((S)-2,6-Dimethylheptanoyloxy)phenyl)-5-(4-nonanoyloxyphenyl)-1,3-pyrimidine The title compound was synthesized in the same manner as in Example 1 except for replacing the {3-dimethylamino-2-(4-decylphenyl)propenylidene}dimethylammonium perchlorate with 3-dimethylamino-2-(4-benzyloxyphenyl)propenylidene}dimethylammonium perchlorate and using pelargonic acid in Example 1-(1).

$^1$H-NMR (CDCl$_3$) δ ppm: 0.90 (9H, m), 1.38 (19H, m), 1.79 (3H, m), 2.60 (2H, t), 2.72 (1H, m), 7.22 (2H, d, J=8.9 Hz), 7.26 (2H, d, J=8.7 Hz), 7.63 (2H, d, J=8.8 Hz), 8.52 (2H, d, J=8.9 Hz), 8.99 (2H, s)

MS (m/e): 544 (M$^+$)

The compound melted at 112.0° C., at which it exhibited an antiferroelectric liquid crystal phase, and changed to an isotropic phase at 168.0° C.

EXAMPLE 9

Synthesis of 2-(4-((S)-2,6-Dimethylheptanoyloxy)phenyl)-5-(4-decyloxycarbonyloxyphenyl)-1,3-pyrimidine The title compound was synthesized in the same manner as in Example 1 except for replacing the {3-dimethylamino- 2-(4-decylphenyl)propenylidene}dimethylammonium perchlorate with 3-dimethylamino-2-(4-benzyloxyphenyl) propenylidene}dimethylammonium perchlorate and using decyl chloroformate in Example 1-(1).

$^1$H-NMR (CDCl$_3$) δ ppm: 0.90 (9H, m), 1.31 (22H, m), 1.56 (1H, m), 1.76 (2H, m), 1.84 (1H, m), 2.72 (1H, m), 4.29 (2H, t), 7.22 (2H, d, J=8.8 Hz), 7.36 (2H, d, J=8.8 Hz), 7.64 (2H, d, J=8.8 Hz), 8.53 (2H, d, J=8.9 Hz), 8.98 (2H, s)

MS (m/e): 588 (M$^+$)

The compound melted at 86.0° C., at which it exhibited an antiferroelectric liquid crystal phase, and changed to an isotropic phase at 146.0° C.

EXAMPLE 10

Synthesis of 2-{4-((S)-2,6-Dimethylheptanoyloxy) phenyl}-5-(4-hexylphenyl)-1,3-pyrimidine The title compound was synthesized in the same manner as in Example 1 except for replacing the {3-dimethylamino-2-(4-decylphenyl)propenylidene}dimethylammonium perchlorate with 3-dimethylamino-2-(4-hexylphenyl) propenylidene}dimethylammonium perchlorate in Example 1-(1) and replacing the (S)-dimethylheptanoic acid with (S)-2-methylhexanoic acid in Example 1-(3).

$^1$H-NMR (CDCl$_3$) δ ppm: 0.90 (9H, m), 1.30 (14H, m), 1.57 (2H, m), 1.66 (1H, m), 1.82 (1H, m), 2.68 (3H, m), 7.22 (2H, d, J=8.8 Hz), 7.34 (2H, d, J=8.3 Hz), 7.54 (2H, d, J=8.2 Hz), 8.52 (2H, d, J=8.9 Hz), 9.00 (2H, s)

The compound melted at 113.0° C., at which it exhibited an antiferroelectric liquid crystal phase, and changed to a smectic A phase at 125.0° C. and then to an isotropic phase at 145.0° C.

EXAMPLE 11

Synthesis of 2-(4'-(S)-2-Methylhexanoyloxy-4-biphenylyl)-5-decyl-1,3-pyrimidine The title compound was synthesized in the same manner as in Example 1 except for replacing the {3-dimethylamino-2-(4-decylphenyl)propenylidene}dimethylammonium perchlorate with 2-decyl-3-ethoxy-2-propenal and replacing the 4-benzyloxybenzamidine hydrochloride with 4-(4-benzyloxyphenyl)benzamidine hydrochloride in Example 1-(1).

$^1$H-NMR (CDCl$_3$) δ ppm: 0.88 (3H, t), 0.95 (3H, t), 1.35 (21H, m), 1.66 (3H, m), 1.82 (1H, m), 2.64 (3H, m), 7.17 (2H, d, J=8.7 Hz), 7.67 (2H, d, J=8.7 Hz), 7.69 (2H, d, J=8.7 Hz), 8.48 (2H, d, J=8.6 Hz), 8.64 (2H, s)

MS (m/e): 500 (M$^+$)

The compound melted at 66.0° C., and changed to an antiferroelectric liquid crystal phase at 87.0° C. via a smectic phase of higher order, a ferroelectric liquid crystal phase at 133.0° C., and then an isotropic phase at 135.0° C.

EXAMPLE 12

Synthesis of 2-4-((S)-2-Methyldecanoloxy)phenyl)-5-(4-decylphenyl)-1,3-pyrimidine The title compound was synthesized in the same manner as in Example 1 except for replacing (S)-2,6-dimethylheptanoic acid used in Example 1-(3) with (S)-2-methyldecanoic acid.

$^1$H-NMR (CDCl$_3$) δ ppm: 0.89 (6H, m), 1.32 (29H, m), 1.53 (1H, m), 1.65 (2H, m), 1.81 (1H, m), 2.70 (3H, m), 7.22 (2H, d, J=11.5 Hz), 7.34 (2H, d, J=8.3 Hz), 7.54 (2H, d, J=10.3 Hz), 8.51 (2H, d, J=11.5 Hz), 8.99 (2H, s)

MS (m/e): 557 (M$^+$ $^+$H)

The compound melted at 101.0° C., at which it exhibited a ferroelectric liquid crystal phase, and changed to an isotropic phase at 130.0° C. When the compound in its ferroelectric liquid crystal phase was cooled, monotropic transition to an antiferroelectric liquid crystal phase was observed immediately before crystallization, but the transition temperature range was too narrow to measure a transition point.

EXAMPLE 13

Synthesis of 2-(4-((S)-2,6-Dimethylheptanoyloxy)-2-fluorophenyl)-5-(4-decyl-3-fluorophenyl)-1,3-pyrimidine The title compound was synthesized in the same manner as in Example 1 except for replacing the {3-dimethylamino-2-(4-decylphenyl)propenylidene}dimethylammonium perchlorate with 3-dimethylamino-2-(4-decyl-3-fluorophenyl) propenylidene}dimethylammonium perchlorate and replacing the 4-benzyloxybenzamidine hydrochloride with 4-benzyloxy-2-fluorobenzamidine hydrochloride in Example 1-(1). 1H-NMR (CDCl$_3$) δ ppm: 0.89 (9H, m), 1.34 (22H, m), 1.86 (4H, m), 2.71 (1H, m), 4.10 (2H, t), 7.04 (2H, m), 7.12 (1H, t), 7.36 (2H, m), 8.20 (1H, t), 9.01 (2H, s)

MS (m/e): 580 (M$^+$)

The compound melted at 71.1° C., at which it exhibited an antiferroelectric liquid crystal phase, and changed to an isotropic phase at 96.5° C.

EXAMPLE 14

Synthesis of 2-(4-((S)-2,6-Dimethylheptanoylthiophenyl-5-4-decylphenyl)-1,3-pyrimidine 1) Synthesis of 2-(4-Dimethylthiocarbamoyloxy)phenyl-5-(4-decylphenyl)-1,3-pyrimidine:

In a 50 ml three-necked flask were charged 1.68 g (4.3 mmol) of 2-(4-hydroxyphenyl)-5-(4-decylphenyl)-1,3-pyrimidine prepared in the same manner as in Example 1-(2), 10 ml of THF, and 10 ml of an aqueous solution of 0.24 g (5.16 mmol) of potassium hydroxide in a nitrogen stream. To the mixture was added dropwise 10 ml of a THF solution containing 0.80 g (6.45 mmol) of dimethylthiocarbamoyl chloride under ice cooling. After the addition, the reaction temperature was raised to room temperature, at which the mixture was stirred for 18 hours. After completion of the reaction, the reaction mixture was washed with a saturated aqueous solution of sodium hydrogencarbonate and extracted with toluene. The organic phase was washed with a saturated aqueous solution of sodium chloride and dried over anhydrous magnesium sulfate. The solvent was removed by evaporation, and the residue was purified by column chromatography using a 10:1 (by volume) mixture of toluene and ethyl acetate as a developing solvent to give 1.26 g of the title compound in a yield of 61%.

2) Synthesis of 2-(4-Mercaptophenyl-5-(4-decylphenyl)-1, 3-pyrimidine:

To a 100 ml three-necked flask was put 1.26 g (2.65 mmol) of 2-(4-(dimethylthiocarbamoyloxy)phenyl-5-(4-decylphenyl)-1,3-pyrimidine and heated to 240° C. by means of a mantle heater, followed by allowing to stand for 18 hours. The IR analysis of the reaction mixture revealed absorption of a carbonyl group. After allowing to cool, 30 ml of diethylene glycol and 0.22 g (4 mmol) of potassium hydroxide were added thereto to conduct reaction at 150° to 170° C. for 1.5 hours. After completion of the reaction, the reaction mixture was poured into ice-water and extracted with chloroform. The resulting aqueous layer was made acidic with 5% hydrochloric acid and extracted with chloroform. The resulting organic layer was dried over anhydrous magnesium sulfate and concentrated. The residue was purified by column chromatography using 30 g of silica gel and a 10:1 (by volume) mixture of toluene and ethyl acetate to give 0.96 g of the title compound in a yield of 90%.

3) Synthesis of 2-(4-((S)-2,6-Dimethylheptanoylthiophenyl)-5-(4-decylphenyl)-1,3-pyrimidine:

In a 100 ml three-necked flask were charged 0.40 g (1 mmol) of 2-(4-mercaptophenyl-5-(4-decylphenyl)-1,3-pyrimidine, 0.17 g (1.2 mmol) of (S)-2,6-dimethylheptanoic acid, 0.372 g (1.8 mmol) of DCC, and 50 ml of dichloromethane in a nitrogen stream, and 0.012 g (0.1 mmol) of 4-dimethylaminopyridine was added thereto, followed by reacting at room temperature for 5 hours. After completion of the reaction, the reaction mixture was filtered and purified by column chromatography using 30 g of silica gel and a 10:1 (by volume) mixture of toluene and ethyl acetate to give 0.46 g of crystals. The resulting crystals were fractionated on an ODS column to afford 0.33 g of the title compound in a yield of 60%.

$^1$H-NMR (CDCl$_3$) δ ppm: 0.89 (9H, m), 1.21–1.45 (22H, m), 1.58 (1H, m), 1.66 (2H, m), 1.82 (1H, m), 2.68 (2H, t), 2.77 (1H, m), 7.34 (2H, d), 7.55 (2H, d), 8.53 (2H, d), 9.02 (2H, s)

MS (m/e): 544 (M$^+$), 404, 141, 113

The compound melted at 91.6° C., at which it exhibited an antiferroelectric liquid crystal phase, and changed to an isotropic phase at 124.4° C.

EXAMPLE 15

Synthesis of 3-(4-((S)-2,6-Dimethylheptanoyloxyphenyl)-6-(4-octyloxyphenyl)-1,2-pyridazine 1) Synthesis of 3-(4-Benzyloxyphenyl)-6-(4-octyloxyphenyl)-1,2-pyridazine:

To a reaction flask were put 0.48 g of magnesium, 5 ml of THF, and a small amount of iodine in a nitrogen stream, and a small portion of a solution of 4.98 g of 4-benzyloxy-1-bromobenzene in 25 ml of THF was added thereto to initiate reaction. Then, the rest of the solution was added thereto dropwise at 35° to 40° C., and the mixture was reacted at the same temperature for 1 hour to prepare a Grignard reagent. To the reaction mixture was added 0.054 g of Ni(Ph$_2$P(CH$_2$)$_3$PPh$_2$)Cl$_2$, and 25 ml of a THF solution containing 3.185 g of 3-chloro-6-(4-octyloxyphenyl)-1,2-pyridazine was added thereto dropwise. After the addition, the reaction was continued at 40° C. for 3 hours. The reaction mixture was poured into ice-water containing diluted hydrochloric acid, and ethyl acetate was added thereto. The organic layer was washed successively with a potassium carbonate aqueous solution and water. The precipitated crystals were collected by filtration, thoroughly washed with ethyl acetate, and dried to give 2.55 g of the title compound.

2) Synthesis of 3-(4-Hydroxyphenyl)-6-(4-octyloxyphenyl)-1,2-pyridazine:

To a reaction flask were put 2.55 g of 3-(4-benzyloxyphenyl)-6-(4-octyloxyphenyl)-1,2-pyridazine, 300 ml of THF, and 30 ml of methanol, and, after displacement with nitrogen, 0.45 g of palladium-carbon was added. The atmosphere was displaced with hydrogen, and the mixture was allowed to react at 50° C. overnight. After completion of the reaction, the reaction mixture was cooled, filtered, and concentrated. Recrystallization of the residue from ethanol yielded 1.43 g of the title compound.

3) Synthesis of 3-(4-((S)-2,6-Dimethylheptanoyloxyphenyl)-6-(4-octyloxyphenyl)-1,2-pyridazine:

The same reaction as in Example 1-(3) was carried out, except for replacing the 5-(4-decylphenyl)-2-(4-hydroxyphenyl)-1,3-pyrimidine with 3-(4-hydroxyphenyl)-6-(4-octyloxyphenyl)-1,2-pyridazine. The resulting crude crystals were recrystallized twice from ethanol to obtain the title compound in a yield of 48.6%.

MS (m/e): 516 (M$^+$), 376, 264, 118

The compound melted at 147.7° C., at which it exhibited an antiferroelectric liquid crystal phase, and changed to an isotropic phase at 195.4° C.

EXAMPLE 16

Synthesis of 2-(4-((S)-2-Methyldecanoyloxy)-3-fluorophenyl)-5-(4-decylphenyl-1,3-pyrimidine The title compound was synthesized in the same manner as in Example 1 except for replacing the (S)-2,6-dimethylheptanoic acid with (S)-2-methyldecanoic acid and replacing the 4-benzyloxybenzamidine hydrochloride with 4-benzyloxy-3-fluorobenzamidine hydrochloride in Example 1-(3).

$^1$H-NMR (CDCl$_3$) δ ppm: 0.89 (6H, m), 1.29 (24H, m), 1.34 (3H, d), 1.44 (2H, m), 1.58 (1H, m), 1.66 (2H, m), 1.82 (1H, m), 2.68 (2H, t), 2.77 (1H, m), 7.24 (1H, d), 7.34 (2H, d), 7.54 (2H, d), 8.31 (2H, m), 8.99 (2H, s)

MS (m/e): 575 (M$^+$ $^+$H), 406

The compound melted at 80.4° C., at which it exhibited an antiferroelectric liquid crystal phase, and changed to a ferroelectric liquid crystal phase at 99.8° C. and then to an isotropic phase at 119.2° C.

EXAMPLE 17

Synthesis of 2-(4-((S)-2-Methylheptanoyloxphenyl)-5-(4-decylphenyl)-1,3-pyrimidine The title compound was synthesized in the same manner as in Example 1 except for replacing the (S)-2,6-dimethylheptanoic acid used in Example 1-(3) with (S)-2-methylheptanoic acid.

$^1$H-NMR (CDCl$_3$) δ ppm: 0.89 (6H, m), 1.32 (23H, m), 1.61 (1H, m), 1.66 (2H, m), 1.81 (1H, m), 2.69 (3H, m), 7.22 (2H, d, J=8.9 Hz), 7.34 (2H, d, J=8.4 Hz), 7.54 (2H, d, J=8.3 Hz), 8.52 (2H, d, J=8.8 Hz), 8.99 (2H, s)

The compound melted at 97.4° C., at which it exhibited an antiferroelectric liquid crystal phase, and changed to a ferroelectric liquid crystal phase at 135.7° C., a smectic A phase at 137° C., and then an isotropic phase at 138° C.

EXAMPLE 18

Synthesis of 2-4-((S)-2-Methyloctanoyloxyphenyl)-5-(4-decylphenyl)-1,3-pyrimidine The title compound was synthesized in the same manner as in Example 1 except for replacing the (S)-2,6-dimethylheptanoic acid used in Example 1-(3) with (S)-2-methyloctanoic acid.

$^1$H-NMR (CDCl$_3$) δ ppm: 0.89 (6H, m), 1.32 (25H, m), 1.61 (1H, m), 1.66 (2H, m), 1.81 (1H, m), 2.68 (3H, m), 7.22 (2H, d, J=8.9 Hz), 7.34 (2H, d, J=8.3 Hz), 7.55 (2H, d, J=8.3 Hz), 8.52 (2H, d, J=8.9 Hz), 9.00 (2H, s)

The compound melted at 101° C., at which it exhibited an antiferroelectric liquid crystal phase, and changed to an isotropic phase at 136° C.

EXAMPLE 19

Synthesis of 2-(4-((S)-2,6-Dimethylheptanoyloxyphenyl)-5-(4-octyloxyphenyl)-1,4-pyrazine The title compound was obtained in the same manner as in Example 15 except for using 3-chloro-6-(4- octyloxyphenyl)-1,4-pyrazine in place of 3-chloro-6-(4-octyloxyphenyl)-1,2-pyridazine.

$^{1}$H-NMR (CDCl$_3$) δ ppm: 0.90 (9H, m), 1.31 (18H, m), 1.58 (1H, m), 1.82 (3H, m), 2.73 (3H, m), 4.04 (2H, t), 7.04 (2H, d, J=8.9 Hz), 7.23 (2H, d, J=8.9 Hz), 8.01 (2H, d, J=9.0 Hz), 8.07 (2H, d, J=8.9 Hz), 9.00 (1H, s), 9.01 (1H, s)

The compound melted at 116° C., at which it exhibited an antiferroelectric liquid crystal phase, and changed to an isotropic phase at 160° C.

EXAMPLE 20

The compounds of the invention were mixed together according to the following formulation to obtain an antiferroelectric liquid crystal composition.

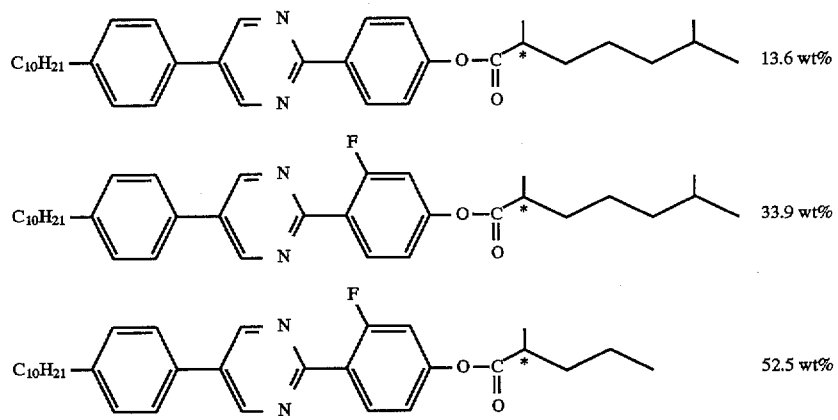

The composition melted at 58.8° C., at which it exhibited an antiferroelectric liquid crystal phase, and changed to a ferroelectric liquid crystal phase at 125.9° C., a smectic A phase at 126.5° C., and then an isotropic phase at 127.5° C. It is seen that mere compounding of a plurality of the compounds of the invention having relative structural similarity brings about a drop of melting point thereby broadening the temperature range of an antiferroelectric liquid crystal phase.

EXAMPLE 21

The compounds of the invention were mixed with known compounds exhibiting an antiferroelectric liquid crystal phase according to the following formulation to obtain an antiferroelectric liquid crystal composition.

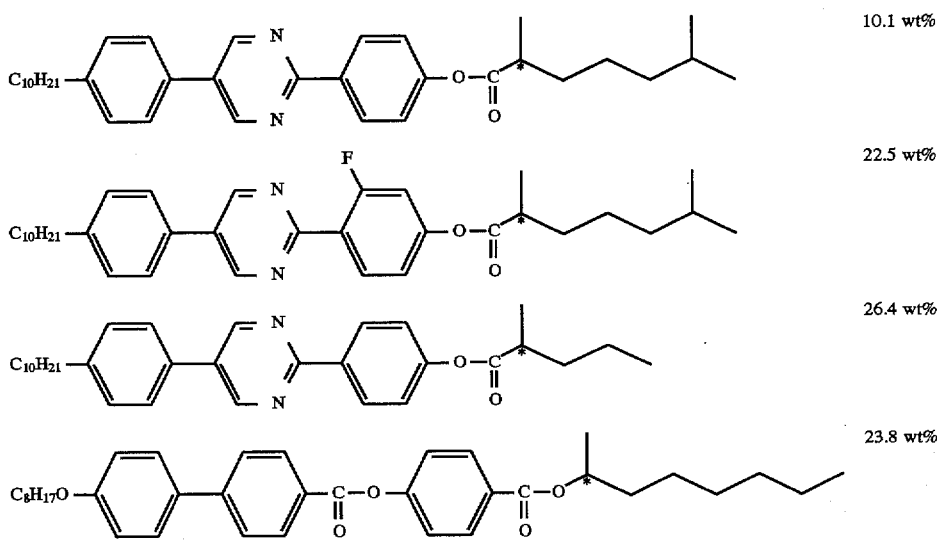

-continued

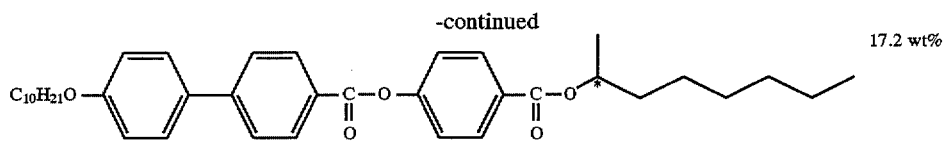

17.2 wt%

The composition melted at 33.9° C., at which it exhibited an antiferroelectric liquid crystal phase, and changed to a smectic A phase at 97.6° C. and then an isotropic phase at 126.3° C. Like this, the compounds of the invention have good miscibility with a known compound exhibiting an antiferroelectric liquid crystal phase or a composition thereof to easily provide an antiferroelectric liquid crystal composition.

EXAMPLE 22

The compounds of the invention were mixed with known compounds exhibiting a smectic C phase or a chiral smectic C phase according to the following formulation to give an antiferroelectric liquid crystal composition.

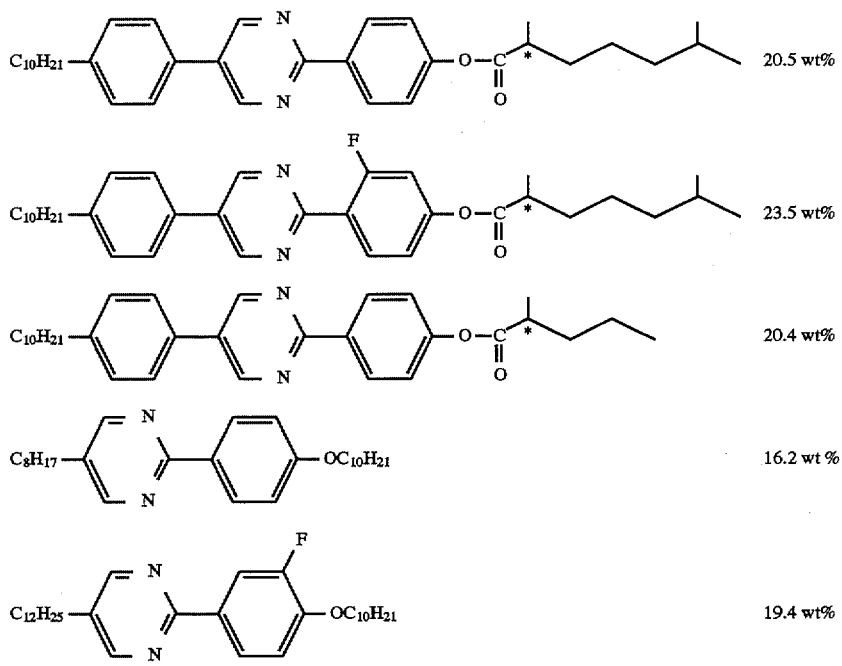

The resulting composition melted at 7.5° C., at which it exhibited an antiferroelectric liquid crystal phase, and changed to a ferroelectric liquid crystal phase at 60° C., and to an isotropic phase at 94.5° C.

Like this, the compounds of the invention have good miscibility with a known compound or composition exhibiting a smectic C phase or a chiral smectic C phase but no antiferroelectric liquid crystal phase thereof to provide an antiferroelectric liquid crystal composition.

EXAMPLE 23

Synthesis of 2-(4'-((S)-2-Methylheptanoyloxy)-3'-fluoro-4-biphenyl-5-nonyl-1,3-pyrimidine 1) Synthesis of 2-(4-Bromophenyl)-5-nonyl-1,3-pyrimidine:

In a 300 ml flask were charged 10 g of 3-dimethylamino-2-nonyl-2-propenal, 10.46 g of 4-bromobenzamidine hydrochloride, and 100 ml of ethanol, and a 28% methanol solution of sodium methoxide was added thereto dropwise, followed by refluxing for 8 hours. After completion of the reaction, ethanol was removed by evaporation, water was added to the residue, and the residue was extracted with toluene. The solvent was removed from the extract by evaporation, and the residue was purified by column chromatography using toluene as a developing solvent to give 4.18 g of the title compound in a yield of 27.7%.

2) Synthesis of 2-(4'-Benzyloxy-3'-fluoro-4-biphenylyl)-5-nonyl-1,3-pyrimidine:

In a 100 ml flask were charged 4.96 g of 4-benzyloxy-3-fluorobromobenzene, 0.442 g of magnesium, and 60 ml of THF in a nitrogen stream, followed by stirring at room temperature for 2 hours to prepare a Grignard reagent.

Separately, 2.0 g of 2-(4-bromophenyl)-5-nonyl-1,3-pyrimidine, 30 ml of THF, and 0.2 g of Ni(Ph$_2$P(CH$_2$)$_3$PPh$_2$)Cl$_2$ were put to a 200 ml flask in a nitrogen stream, and the above prepared Grignard reagent was added thereto dropwise, followed by stirring at room temperature for 20 hours. After completion of the reaction, the reaction solution was poured into a saturated aqueous solution of ammonium chloride and extracted with toluene. The solvent was removed from the extract by evaporation, and the residue was subjected to column chromatography using toluene as a developing solvent to give 2.3 g of the title compound in a yield of 43.38%.

3) Synthesis of 2-(4'-Hydroxy-3'-fluoro-4-biphenylyl)-5-nonyl-1,3-pyrimidine:

In a 100 ml flask were charged 2.3 g of 2-(4'-benzyloxy-3'-fluoro-4-biphenylyl)-5-nonyl-1,3-pyrimidine, 40 ml of methanol, and 40 ml of THF, and 0.4 g of palladium-carbon was added thereto to conduct hydrogenation at 40° C. for 8 hours. After completion of the reaction, palladium-carbon was removed by filtration, and the filtrate was subjected to column chromatography using a 5:1 mixture (by volume) of toluene and ethyl acetate as a developing solvent to obtain 1.0 g of the title compound in a yield of 62.5%.

4) Synthesis of 2-(4'-((S)-2-Methylheptanoyloxy)-3'-fluoro-4-biphenylyl)-5-nonyl-1,3-pyrimidine:

In a 50 ml flask were charged 0.5 g of 2-(4'-hydroxy-3'-fluoro-4-biphenylyl)-5-nonyl-1,3-pyrimidine, 1.5 g of (S)-2-methylheptanoic acid, 0.36 g of DCC, and 10 ml of dichloromethane, and a catalytic amount of 4-dimethylaminopyridine was added thereto, followed by reacting at room temperature for 2 hours. After completion of the reaction, the reaction mixture was filtered and purified by column chromatography using a 10:1 mixture (by volume) of toluene and ethyl acetate to obtain 0.5 g of crystals. The resulting crystals were fractionated on an ODS column to recover 0.35 g of the title compound in a yield of 75.71%.

$^1$H-NMR (CDCl$_3$) δ ppm: 0.90 (6H, m), 1.33 (19H, m), 1.44 (2H, m), 1.66 (3H, m), 1.83 (1H, m), 2.64 (2H, t), 2.76 (1H, m), 7.20 (1H, m), 7.44 (2H, m), 7.67 (2H, d, J=8.8 Hz), 8.49 (2H, d, J=8.8 Hz), 8.65 (2H, s)

MS (m/e): 519 (M$^+$ $^+$H)

The compound melted at 43.5° C., at which it exhibited an antiferroelectric liquid crystal phase, and changed to isotropic liquid at 130.6° C. It is seen that the compound having fluorine in the core thereof exhibits an antiferroelectric liquid crystal phase over a very broad temperature range and that the compound of formula (I) in which R$^2$ has a straight-chain alkyl group containing 3 or more carbon atoms stably exhibits an antiferroelectric liquid crystal phase.

EXAMPLE 24

Synthesis of 2-(4'-((S)-2-Methylhexanoyloxy)-4-biphenylyl)-5-nonyl-1,3-pyrimidine The title compound was obtained in the same manner as in Example 23 except for replacing the 4-benzyloxy-3-fluorobromobenzene with 4-benzyloxybromobenzene and replacing the (S)-2-methylheptanoic acid with (S)-2-methylhexanoic acid. Yield: 46.2%.

$^1$H-NMR (CDCl$_3$) δ ppm: 0.88 (3H, t), 0.94 (3H, t), 1.36 (19H, m), 1.59 (1H, m), 1.67 (2H, m), 1.87 (1H, m), 2.63 (2H, t), 2.71 (1H, m), 7.17 (2H, d, J=8.8 Hz), 7.67 (2H, d, J=8.8 Hz), 7.69 (2H, d, J=8.8 Hz), 8.48 (2H, d, J=8.7 Hz), 8.64 (2H, s)

MS (m/e): 486 (M$^+$)

The compound melted at 73.3° C. and exhibited a smectic phase of high order having a mosaic texture, and changed to an antiferroelectric liquid crystal phase at 88.1° C., to a chiral smectic C phase at 102.6° C., and to an isotropic phase at 138° C. Like this, the compound of formula (I) in which R$^2$ has a straight-chain alkyl group containing 3 or more carbon atoms stably exhibits an antiferroelectric liquid crystal phase.

COMPARATIVE EXAMPLE 1

Synthesis of 5-(4-(2,6-Dimethylheptanoyloxy) phenyl)-2-(4-decylphenyl)-1,3-pyrimidine 1) Synthesis of 2-(4-Decylphenyl)-5-(4-benzyloxyphenyl)-1,3-pyrimidine (Compound 1c-1):

In a 200 ml three-necked flask were charged 6.05 g (14.8 mmol) of {3-dimethylamino-2-(4-benzyloxyphenyl) propenylidene}-dimethylammonium perchlorate, 4.0 g (13.5 mmol) of 4-decylbenzamidine hydrochloride, and 130 ml of ethanol in a nitrogen stream, and 7.82 g of a 28% methanol solution of sodium methoxide was added thereto dropwise with 20 ml of ethanol under cooling with ice. After the addition, the reaction was continued at an ethanol refluxing temperature for 24 hours. After completion of the reaction, the reaction mixture was poured into 200 ml of water, followed by filtration. The precipitated crystals as collected on the filter paper were washed with toluene and dried to give 4.50 g of the title compound in a yield of 70%.

2) Synthesis of 2-(4-Decylphenyl)-5-(4-hydroxyphenyl)-1,3-pyrimidine (Compound 1c-2):

In a 300 ml four-necked flask were charged 3.70 g (9.5 mmol) of compound 1c-1, 50 ml of methanol, and 100 ml of THF, and 0.74 g of palladium-carbon was added thereto to conduct hydrogenation at 50° C. for 3 hours. After completion of the reaction, palladium-carbon was removed by filtration, and the filtrate was subjected to column chromatography using 50 g of silica gel and toluene to afford 2.20 g of the title compound in a yield of 60%.

3) Synthesis of 5-(4-(2,6-Dimethylheptanoyloxy)phenyl)-2-(4-decylphenyl)-1,3-pyrimidine:

In a 200 ml four-necked flask were charged 1.74 g (4.5 mmol) of compound 1c-2, 0.78 g (4.9 mmol) of (S)-2,6-dimethylheptanoic acid, 1.20 g (5.8 mmol) of DCC, and 50 ml of dichloromethane in a nitrogen stream, and 0.05 g (0.4 mmol) of 4-dimethylaminopyridine was added thereto, followed by reacting at room temperature for 4 hours. After completion of the reaction, the reaction mixture was filtered and purified by column chromatography using 80 g of silica gel and a 10:1 mixture (by volume) of toluene and ethyl acetate to afford 2.22 g of crystals. Recrystallization from 40 ml of ethanol and 5 ml of chloroform gave 2.22 g of the title compound in a yield of 94%.

$^1$H-NMR (CDCl$_3$) δ ppm: 0.87 (9H, m), 1.24 (14H, m), 1.26 (2H, m), 1.31 (4H, m), 1.34 (1H, m), 1.43 (2H, m), 1.67 (2H, m), 1.81 (1H, m), 2.70 (3H, m), 7.24 (2H, d), 7.32 (2H, d), 7.63 (2H, d), 8.38 (2H, d, J=10.3 Hz), 8.98 (2H, s)

MS (m/e): 528 (M$^+$)

The compound melted at 109.8° C., exhibited only an Sc* phase, and changed to an isotropic phase at 126.4° C. An antiferroelectric liquid crystal phase was not exhibited either in a temperature rise or drop. Accordingly, it is understood that a compound whose core (i.e., 2,5-diphenylpyrimidine skeleton) is the same as that of the compound of Example 1 but different in direction it faces is unfavorable.

COMPARATIVE EXAMPLE 2

Synthesis of 2-(4-(2-Fluoro-2-methylheptanoyloxy) phenyl)-5-(4-decylphenyl)-1,3-pyrimidine The title compound was obtained in the same manner as in Example 1 except for replacing the (S)-2,6-dimethylheptanoic acid used in Example 1-(3) with (S)-2-fluoro-2-methylheptanoic acid. Yield: 35%.

$^1$H-NMR (CDCl$_3$) δ ppm: 0.88 (3H, t), 0.92 (3H, t), 1.34 (20H, m), 1.55 (4H, m), 1.74 (3H, J=21.2 Hz), 2.68 (2H, t), 7.26 (2H, d, J=8.9 Hz), 7.34 (2H, d, J=8.3 Hz), 7.55 (2H, d, J=8.2 Hz), 8.55 (2H, d, J=8.9 Hz), 9.00 (2H, s)

MS (m/e): 532 (M$^+$)

The compound melted at 73.3° C., at which it exhibited a ferroelectric liquid crystal phase, and changed to a smectic A phase at 109° C. and to an isotropic phase at 117.5° C. An antiferroelectric liquid crystal phase was not exhibited. Although the difference of this compound from the compound of Example 1 is only the structure of the chiral site, it is seen that such a structural modification results in disappearance of an antiferroelectric liquid crystal phase and is unfavorable.

COMPARATIVE EXAMPLE 3

Synthesis of 2-(4-((S)-2-Methylbutyryloxy)phenyl)-5-(4-decylphenyl)-1,3-pyrimidine The title compound was synthesized in the same manner as in Example 1 except for replacing the (S)-2,6-dimethylheptanoic acid used in Example 1-(3) with (S)-2-methylbutanoic acid.

$^1$H-NMR (CDCl$_3$) δ ppm: 0.88 (3H, t), 1.05 (3H, t), 1.50 (17H, m), 1.65 (3H, m), 1.85 (1H, m), 2.68 (2H, m), 7.22 (2H, d, J=8.9 Hz), 7.33 (2H, d, J=8.3 Hz), 7.54 (2H, d, J=8.9 Hz), 8.52 (2H, d, J=8.9 Hz), 9.00 (2H, s)

MS (m/e): 472 (M$^+$)

The compound melted at 103.7° C., at which it exhibited an unidentified smectic phase of high order, and changed to a ferroelectric liquid crystal phase (Sc* phase) at 117° C., a smectic A phase at 160° C., and then an isotropic phase at 176° C. No antiferroelectric liquid crystal phase was exhibited. Like this, a compound having the same formula as formula (I) except that R$^2$ is C$_2$H$_5$ does not exhibit an antiferroelectric liquid crystal phase.

COMPARATIVE EXAMPLE 4

Synthesis of 2-(4-((S)-2-Methylbutyryloxy)phenyl-5-(4-octylphenyl)-1,3-pyrimidine The title compound was obtained in the same manner as in Example 1 except for replacing the 5-(4-decylphenyl)-2-(4-hydroxyphenyl)-1,3-pyrimidine with 5-(4-octylphenyl)-2-(4-hydroxyphenyl)-1,3-pyrimidine and replacing the (S)-2,6-dimethylheptanoic acid with (S)-2-methylbutanoic acid in Example 1-(3). Yield: 95.1%.

$^1$H-NMR (CDCl$_3$) δ ppm: 0.89 (3H, t), 1.05 (3H, t), 1.31 (13H, m), 1.66 (3H, m), 1.87 (1H, m), 2.68 (3H, m), 7.22 (2H, d, J=9.0 Hz), 7.34 (2H, d, J=8.4 Hz), 7.54 (2H, d, J=8.4 Hz), 8.52 (2H, d, J=9.0 Hz), 9.00 (2H, s)

MS (m/e): 446 (M$^+$ $^+$H)

The compound is the one disclosed in JP-A-63-170367. The publication mentions that the compound melts at 116° C. to exhibit a chiral smectic C phase and exhibits transition to a smectic A phase at 161° C. and then to an isotropic phase at 176° C. It is also mentioned that on cooling from the state showing a chiral smectic C phase a smectic X phase monotropically appears at 119° C.

Hence the inventors investigated the smectic X phase, which is a higher order phase of the chiral smectic C phase, of the above synthesized compound. When observed under a polarizing microscope, the smectic X phase showed a mosaic texture, which is to be observed in neither a ferroelectric smectic C phase nor an antiferroelectric smectic C phase but is to be observed in liquid crystal phases of higher order, such as a smectic B phase.

A transparent conducting film was provided on a glass substrate, and a polyvinyl alcohol orientation membrane was formed thereon and rubbed. A pair of the thus prepared substrates were assembled, with the rubbing direction of the upper orientation membrane and that of the lower one being parallel to each other, into a liquid crystal cell having a cell thickness of 2.3 μm. The compound was injected into the cell, and phase transition was observed with a voltage applied. A smectic A phase and then a ferroelectric chiral smectic C phase were observed in the order of from high to low temperature, and a response of a ferroelectric chiral smectic phase was observed in the further lower temperature side. Accordingly, the smectic X phase as observed with this compound was found to be a tilt phase of smectic B phase series but not to be an antiferroelectric liquid crystal phase.

COMPARATIVE EXAMPLE 5

Synthesis of 2-(4-((S)-2-Methylbutyryloxy)phenyl)-5-(4-octyloxyphenyl)-1,3-pyrimidine The title compound was obtained in the same manner as in Example 1 except for replacing the {3-dimethylamino-2-(4-decylphenyl)propenylidene}dimethylammonium perchlorate used in Example 1-(1) with 3-dimethylamino-2-(4-octyloxyphenyl)propenylidene}dimethylammonium perchlorate and replacing the (S)-2,6-dimethylheptanoic acid used in Example 1-(3) with (S)-2-methylbutanoic acid.

$^1$H-NMR (CDCl$_3$) δ ppm: 0.89 (3H, t), 1.05 (3H, t), 1.21 (11H, m), 1.45 (2H, m), 1.67 (1H, m), 1.85 (3H, m), 2.65 (1H, m), 4.02 (2H, t), 7.04 (2H, d, J=8.8 Hz), 7.22 (2H, d, J=8.8 Hz), 7.55 (2H, d, J=8.8 Hz), 8.51 (2H, d, J=8.9 Hz), 8.97 (2H, s)

MS (m/e): 460 (M$^+$)

The compound is the one disclosed in JP-A-63-170367. The publication mentions that the compound melts at 59° C. to exhibit a smectic X phase and shows phase transitions to a smectic Y phase at 76° C., a smectic Z phase at 115° C., a chiral smectic C phase at 120° C., a smectic A phase at 161° C., and then an isotropic phase at 176° C.

The inventors investigated the smectic X to Z phases, which are higher order phases of the chiral smectic C phase, of the above synthesized compound. When observed under a polarizing microscope, the smectic Z phase showed a mosaic tissue, which is to be observed in neither a ferroelectric smectic C phase nor an antiferroelectric smectic C phase but is to be observed in liquid crystal phases of higher order, such as a smectic B phase. Accordingly, it was confirmed that the smectic Z phase as observed with this compound was a tilt phase of smectic B phase series and the smectic X and Y phases are each of the further higher order so that any of the smectic X to Z phases is not an antiferroelectric liquid crystal phase.

COMPARATIVE EXAMPLE 6

Synthesis of 2-(4'-((S)-2-Methylbutyryloxy)-4-biphenylyl)-5-nonyl-1,3-pyrimidine The title compound was obtained in the same manner as in Example 24 except for replacing the (S)-2-methylheptanoic acid with (S)-2-methylbutanoic acid. Overall yield: 43.8%.

$^1$H-NMR (CDCl$_3$) δ ppm: 0.88 (3H, t), 1.05 (3H, t), 1.32 (15H, m), 1.67 (3H, m), 1.87 (1H, m), 2.64 (3H, m), 7.17 (2H, d, J=8.8 Hz), 7.67 (2H, d, J=8.9 Hz), 7.69 (2H, d, J=8.7 Hz), 8.48 (2H, d, J=8.7 Hz), 8.64 (2H, s)

MS (m/e): 458 (M$^+$)

The compound is the one disclosed in JP-A-3-12478. The compound melts at 82.3° C. to exhibit a smectic phase of higher order having a mosaic texture and changes to an Sc* phase at 98.1° C., to a chiral nematic phase (cholesteric phase) at 152.3° C., and then to an isotropic phase at 154° C. Seeing that the smectic phase of higher order, which was observed on the lower temperature side of the ferroelectric chiral smectic C phase, showed a mosaic texture similarly to the compound of Comparative Example 4, it is a phase of higher order such as a smectic B phase but not an antiferroelectric liquid crystal phase.

EXAMPLE 25

Synthesis of 2-{2-Fluoro-4-((S)-2,6-dimethylheptanoyloxy)phenyl}-5-(4-decyloxy-3-fluorophenyl)-pyridine 1) Synthesis of 2-Fluoro-4-benzyloxybromobenzene:

A mixture of 64.6 g (338 mmol) of 2-fluoro-4-hydroxybromobenzene, 53.1 g (389 mmol) of benzyl chloride, 93.3 g (676 mmol) of potassium carbonate and 150 ml of DMF was heated to a temperature of 80° C. for 2 hours. After cooled, the reaction mixture was poured into water. The reaction mixture was then extracted with ethyl acetate. The resulting organic layer was washed with saturated brine, and then dried over magnesium sulfate anhydride. After dried, the material was distilled under reduced pressure (120°–122° C./2 mmHg) to obtain 52.5 g of the title compound (yield: 55.3%).

2) Synthesis of 2-Fluoro-4-benzyloxyphenylboronic acid:

A solution of 5.62 g (20 mmol) of the bromo compound obtained in the foregoing synthesis step (1) in 60 ml of ethyl ether was cooled to a temperature of −72° C. To the solution was then added dropwise 18.8 ml (30 mmol) of n-butyl lithium. The reaction mixture was then stirred at the same temperature for 2 hours. Subsequently, to the reaction mixture was added dropwise a solution of 2.39 g (22 mmol) of trimethoxyborane in 5 ml of ether at the same temperature. The reaction mixture was stirred at the same temperature for 1 hour, at a temperature of from −72° C. to room temperature for 1 hour and at room temperature for 1 hour. Subsequently, the reaction mixture was acidified with dilute hydrochloric acid. The reaction mixture was extracted with ethyl acetate, washed with saturated brine, and then dried over magnesium sulfate anhydride. The resulting crystal was then recrystallized from n-hexane to obtain 2.85 g of the title compound (Yield: 57.9%).

3) Synthesis of 3-Fluoro-4-decyloxybromobenzene:

The synthesis procedure of the foregoing synthesis step (1) was followed except that 50 g (262 mmol) of 3-fluoro-4-hydroxybromobenzene, 69.4 g (314 mmol) of decyl bromide, 72.2 g (524 mmol) of potassium carbonate and 150 ml of DMF were used. As a result, 50.4 g of the title compound was obtained (yield: 58.1%).

4) Synthesis of 5-(4-Decyloxy-3-fluorophenyl)-2-benzyloxypyridine:

3.08 g (127 mmol) of magnesium, 60 ml of THF and a small amount of iodine were charged into a reaction flask in a stream of nitrogen. Subsequently, a solution of 40 g of 3-fluoro-4-decyloxybromobenzene in 60 ml of THF was partly added dropwise to the reaction solution to initiate reaction. The remainder of the solution was then added dropwise to the reaction mixture at a temperature of from 35° C. to 40° C. After the completion of the dropwise addition, the reaction mixture was allowed to undergo reaction at the same temperature for 2 hours, and then cooled to obtain a Grignard reagent. Subsequently, 25.2 g (115 mmol) of 2-benzyloxy-5-chloropyridine, 100 ml of THF and 0.5 g of $Ni(Ph_2P(CH_2)_2PPh_2)Cl_2$ were charged into a reaction flask the air in which had been replaced by nitrogen. The foregoing Grignard reagent was then added dropwise to the reaction mixture at the same temperature in 20 minutes. After the completion of the dropwise addition, the reaction mixture was allowed to undergo reaction at a temperature of 60° C. for 3 hours. The reaction product was then put into an aqueous solution of ammonium chloride. The reaction product was extracted with a 1:1 (by volume) mixture of toluene and ethyl acetate, and then dried. The reaction product was then purified by silica gel column chromatography to obtain 24.5 g of the title compound (yield: 49%).

5) Synthesis of 5-(3-Fluoro-4-decylphenyl)-2-hydroxypyridine:

14.0 g of 2-benzyloxy-5-(3-fluoro-4-decylphenyl) pyridine, 50 ml of THF, 15 ml of methanol and 2 g of 10% palladium-carbon were charged into a reaction flask. The reaction mixture was then allowed to undergo hydrogenation at room temperature under ordinary pressure for 48 hours. After the completion of the reaction, the reaction product was purified by column chromatography to obtain 12.3 g of the title compound (yield: 32.5%).

6) Synthesis of 2-chloro-5-(3-fluoro-4-decylphenyl) pyridine:

3.27 g of 5-(4-decylphenyl)-2-hydroxypyridine, 8 ml of phosphorus oxychloride and 4.24 g of diethylaniline were charged into a reaction flask. The reaction mixture was then allowed to undergo reaction at a temperature of 100° C. for 24 hours. After the completion of the reaction, the reaction product was cooled, gradually put into ice water, and then extracted with ethyl acetate. The resulting organic layer was washed with saturated brine, and then dried over magnesium sulfate anhydride. The solvent was then distilled off to obtain a crude product. The crude product was then subjected to column chromatography to obtain 1.6 g of the title compound (yield: 46.5%).

7) Synthesis of 2-(2-Fluoro-4-benzyloxyphenyl)-5-(4-decyloxy-3-fluorophenyl)pyridine:

To a mixture of 1.12 g of 2-fluoro-4-benzyloxy phenylboronic acid, 1.5 g of chloropyridine obtained in the foregoing synthesis step (6), 0.25 g of sodium hydroxide and 0.14 g of tetrakis(triphenylphosphine)palladium were added 38 ml of dimethoxyethane and 5.5 ml of deaerated water in a stream of nitrogen. The mixture was then stirred at a temperature of 80° C. overnight. The reaction mixture was then cooled. To the reaction mixture was then added 50 ml of ethyl acetate. The reaction mixture was then hot-filtered. The solvent was then distilled off. The reaction product was then purified by column chromatography to obtain 1.55 g of the title compound (yield: 70.8%).

8) Synthesis of 2-(2-Fluoro-4-hydroxyphenyl)-5-(4-decyloxy-3-fluorophenyl)pyridine:

A mixture of 1.13 g of the benzyl compound obtained in the foregoing synthesis step (7), 0.34 g of 10% palladium-carbon, 15 ml of THF and 4 ml of methanol was allowed to undergo hydrogenation at a temperature of 40° C. under ordinary pressure for 40 hours. After the completion of the reaction, the reaction product was purified by column chromatography to obtain 0.66 g of the title compound (yield: 96.0%).

9) Synthesis of 2-(3-fluoro-4-((S)-2,6-dimethylheptanoyloxy)phenyl)-5-(4-decylphenyl)pyridine:

The procedure of Example 1 (3) was followed to obtain the title compound except that 2-(2-fluoro-4-hydroxyphenyl)-5-(4-decyloxy-3-fluorophenyl)pyridine was used instead of 5-(4-decylphenyl)-2-(4-hydroxyphenyl)-1,3-pyrimidine. (Yield: 76.9%)

$^1$H-NMR (CDCl$_3$) δ ppm: 0.89 (9H, m), 1.2–1.51 (20H, m), 1.56–1.58 (3H, m), 1.84–1.87 (3H, m), 2.70–2.72 (1H, m), 4.09 (2H, t), 6.97–7.09 (3H, m), 7.33–7.39 (3H, m), 7.85–7.88 (2H, m), 8.04–8.11 (1H, m), 8.89 (1H, s)

MS (m/e): 579 (M$^+$)

This product melted at 53.5° C. at which it exhibited an antiferroelectric liquid crystal phase and changed to an isotropic phase at 86.6° C.

EXAMPLE 26

Synthesis of 2-{4-((S)-2,6-Dimethylheptanoyloxy)phenyl}-5-(4-decyloxyphenyl)-pyridine The procedure of Example 21 was followed to synthesize the title compound.

$^1$H-NMR (CDCl$_3$) δ ppm: 0.89 (9H, m), 1.23–1.33 (20H, m), 1.57–1.58 (3H, m), 1.80–1.83 (3H, m), 2.71–2.73 (1H, m), 4.01 (2H, t), 7.02 (2H, d, J=8.8 Hz), 7.20 (3H, d, J=8.8 Hz), 7.56 (2H, d, J=8.8 Hz), 7.75 (2H, d), 7.89 (2H, d), 8.05 (2H, d, J=8.8 Hz), 8.88 (1H, s)

MS (m/e): 543 (M$^+$ $^+$H)

This compound melted at 105.1° C. and changed to an antiferroelectric phase at 135.7° C. via a smectic phase of higher order and then an isotropic phase at 86.6° C.

EXAMPLE 27

Synthesis of 2-(4-((S)-2,6-Dimethylheptanoyloxy)-2-fluorophenyl)-5-(4-octyloxy-3-fluorophenyl)-1,3-pyrimidine The synthesis procedure of Example 1-(1) was followed except that {3-dimethylamino-2-(4-octyloxy-3-fluorophenyl)propenylidene}dimethylammonium perchlorate was used instead of {3-dimethylamino-2-(4-decylphenyl)propenylidene}dimethylammonium perchlorate and 4-benzyloxy-2-fluorobenzamidine hydrochloride was used instead of 4-benzyloxybenzamidine hydrochloride.

$^1$H-NMR (CDCl$_3$) δ ppm: 0.88–0.91 (9H, m), 1.23–1.36 (16H, m), 1.53–1.59 (3H, m), 1.84–1.88 (3H, m), 2.71–2.72 (1H, m), 4.10 (2H, t), 7.02–7.04 (2H, m), 7.11–7.13 (1H, m), 7.36–7.39 (2H, m), 8.17–8.22 (1H, m), 9.01 (2H, s)

MS (m/e): 552 (M$^+$)

This compound melted at 84° C., at which it exhibited an antiferroelectric liquid crystal phase and changed to an isotropic phase at 99° C.

EXAMPLE 28

Synthesis of 2-{4-((S)-2,6-Dimethylheptanoyloxy)phenyl}-5-(4-octyloxyphenyl)-1,3-pyrimidine The synthesis procedure of Example 1 (1) was followed except that {3-dimethylamino-2-(4-octyloxyphenyl)propenylidene}dimethylammonium perchlorate was used instead of {3-dimethylamino-2-(4-decylphenyl)propenylidene}dimethylammonium perchlorate.

$^1$H-NMR (CDCl$_3$) δ ppm: 0.88–0.91 (9H, m), 1.23–1.36 (16H, m), 1.53–1.59 (3H, m), 1.84–1.88 (3H, m), 2.70–2.73 (1H, m), 4.10 (2H, t), 7.04 (2H, d, J=8.8 Hz), 7.21 (3H, d, J=8.9 Hz), 7.55 (2H, d, J=8.9 Hz), 8.51 (2H, d, J=8.8 Hz), 8.96 (2H, s)

MS (m/e): 516 (M$^+$)

This compound melted at 111° C., and changed to an antiferroelectric liquid crystal phase, a ferroelectric liquid crystal phase at 154° C., a smectic A phase at 155° C., and then an isotropic phase at 156° C.

EXAMPLE 29

Synthesis of 2-(4-((S)-2-Methylheptanoyloxy)phenyl)-5-(4-octyloxycarbonyloxyphenyl)-1,3-pyrimidine 1) Synthesis of 5-(4-Benzyloxyphenyl)-2-(4-hydroxyphenyl)-1,3-pyrimidine:

3.93 g (10.0 mmol) of {3-dimethylamino-2-(4-benzyloxyphenyl)propenylidene}dimethylammonium perchlorate, 1.38 g (8.0 mmol) of 4-hydroxybenzamidine hydrochloride and 100 ml of ethanol were charged into a 200-ml three-necked flask. To the reaction mixture was then added dropwise 5.79 g of a 28% methanol solution of sodium methoxide with 20 ml of ethanol under cooling with ice. After the completion of dropwise addition, the reaction mixture was allowed to undergo reaction at the reflux temperature of ethanol for 22 hours. After the completion of the reaction, the reaction product was put into 100 ml of ice water. The crystal thus precipitated was filtered. The crystal on the filter paper was washed with methanol, and then dried to obtain 2.39 g of the title compound (yield: 84.5%).

2) Synthesis of 5-(4-Benzyloxyphenyl)-2-(4-(S)-2-methylheptanoyloxyphenyl)-1,3-pyrimidine:

A mixture of 0.80 g (2.26 mmol) of the compound obtained in the foregoing synthesis step (1), 0.76 g (5.60 mmol) of (S)-2-methylheptanoic acid, 2.00 g (10.0 mmol) of DCC, 0.028 g (0.226 mmol) of 4-dimethylaminopyridine, 30 ml of THF and 20 ml of methylene chloride was stirred at room temperature for 6 hours. After stirring, the solvent was distilled off. The residue was then purified by column chromatography to obtain 0.93 g of the title compound (yield: 86.1%).

3) Synthesis of 5-(4-Hydroxyphenyl)-2-(4-(S)-2-methylheptanoyloxyphenyl)-1,3-pyrimidine:

A mixture of 0.90 g of the compound obtained in the foregoing synthesis step (2), 0.18 g of palladium-carbon and 20 ml of THF was allowed to undergo hydrogenation at room temperature under ordinary pressure for 45 hours. After the completion of the reaction, the reaction product was purified by column chromatography to obtain 0.36 g of the title compound (yield: 50.0%).

4) Synthesis of 5-(4-Octyloxycarbonyloxyphenyl)-2-(4-(S)-2-methylheptanoyloxyphenyl)-1,3-pyrimidine:

To a solution obtained by mixing 0.36 g (0.923 mmol) of the compound obtained in the foregoing synthesis step (3), 0.44 g (5.55 mmol) of pyridine, 10 ml of THF and 5 ml of methylene chloride was added dropwise 0.21 g (1.11 mmol) of octyl chloroformate at a temperature of 0° C. The reaction mixture was then stirred at the same temperature for 1 hour. After stirring, water was added to the reaction product at a temperature of 0° C. The reaction product was extracted with methylene chloride, dried over magnesium sulfate anhydride, and then purified by column chromatography to obtain 0.26 g of the title compound (yield: 52.0%).

$^1$H-NMR (CDCl$_3$) δ ppm: 0.91 (6H, m), 1.31 (3H, d), 1.28–1.37 (12H, m), 1.39–1.45 (4H, m), 1.61 (1H, m), 1.75–1.90 (3H, m), 2.72 (1H, m), 4.29 (2H, t), 7.22 (2H, d, J=9.0 Hz), 7.34 (2H, d, J=8.8 Hz), 7.64 (2H, d, J=8.8 Hz), 8.52 (2H, d, J=9.0 Hz), 8.99 (2H, s)

MS (m/e): 546 (M$^+$)

This compound melted at 86.5° C., at which it exhibited an antiferroelectric phase and changed to an isotropic phase at 153.5° C.

EXAMPLE 30

Synthesis of 2-(4-((S)-2,6-Dimethylheptanoyloxy)phenyl)-5-(4-decyloxycarbonylphenyl)-1,3-pyrimidine 1) Synthesis of 2-(4-benzyloxyphenyl)-5-(4-decyloxycarbonylphenyl)-1,3-pyrimidine:

To 0.80 g (2.1 mmol) of 5-(4-carboxyphenyl)-2-(4-benzyloxyphenyl)pyrimidine were added 6 ml of 1,2-dichloroethane and 0.7 mg of benzyltriethylammonium chloride. The reaction mixture was then heated under reflux. To the reaction mixture was then added 2 ml of thionyl chloride. The reaction mixture was then heated under reflux for 20 hours. After refluxing, the solvent and thionyl chloride used were distilled off under reduced pressure to obtain an acid chloride. Subsequently, to a solution obtained by mixing 0.398 g (2.52 mmol) of 1-decanol, 10 ml of THF and 1.00 g (12.6 mmol) of pyridine was added the foregoing acid chloride in the form of THF suspension at a temperature of 0° C. The reaction mixture was then stirred for 10 minutes. The reaction mixture was brought to room temperature where it was then stirred for 60 hours. After stirring, water was added to the reaction product. The resulting insoluble precipitates were filtered off and the separated organic layer was dried over anhydrous magnesium sulfate. The reaction product thus dried was then purified by column chromatography to obtain 0.37 g of the title compound (yield: 33.7%).

2) Synthesis of 5-(4-(Decyloxycarbonyl)phenyl)-2-(4-hydroxyphenyl)pyrimidine:

0.37 g of the ester obtained in the foregoing synthesis step (1) was added to 7 ml of THF. To the mixture were then added 0.11 g of palladium-carbon and 3 ml of methanol. The reaction mixture was then allowed to undergo hydrogenation at a temperature of 40° C. under ordinary pressure for 24 hours. Subsequently, palladium-carbon was removed by filtration. The residue was then purified by column chromatography to obtain 0.15 g of the title compound (yield: 48.3%).

3) Synthesis of 5-(4-((Decyloxycarbonyl)phenyl)-2-(4-((S)-2,6-dimethylheptanoyloxy)phenyl)pyrimidine:

To 0.22 g (1.42 mmol) of (S)-2,6-dimethylheptanoic acid and the hydroxy compound obtained in the foregoing synthesis step (2) were added 10 ml of methylene chloride and 3 ml of THF. To the mixture were then added 0.44 g (2.13 mmol) of DCC and a small amount of 4-dimethylaminopyridine. The reaction mixture was then stirred for 1 hour. The resulting salt was withdrawn by filtration, and then purified by column chromatography to obtain 50 mg of the title compound.

$^1$H-NMR (CDCl$_3$) δ ppm: 0.89 (9H, m), 1.24–1.44 (19H, m), 1.33 (3H, d), 1.55–1.63 (3H, m), 1.78–1.82 (3H, m), 2.70–2.74 (1H, m), 4.36 (2H, t), 7.24 (2H, d), 7.71 (2H, d), 8.20 (2H, d), 8.54 (2H, d), 9.04 (2H, s)

MS (m/e): 573 (M$^+$ $^+$H)

This compound melted at 99° C., at which it exhibited an antiferroelectric phase and changed to an isotropic phase at 107° C.

As has been fully described and demonstrated, many of the liquid crystal compounds of the invention exhibit a very stable antiferroelectric liquid crystal phase and are useful in electrooptical devices using antiferroelectric liquid crystals. Further, the compounds of the invention have good compatibility with many known antiferroelectric liquid crystal compounds to provide liquid crystal materials having improved temperature characteristics.

While the invention has been described in detail and with reference to specific examples thereof, it will be apparent to one skilled in the art that various changes and modifications can be made therein without departing from the spirit and scope thereof.

What is claimed is:
1. A antiferro-electric liquid crystal compound represented by formula:

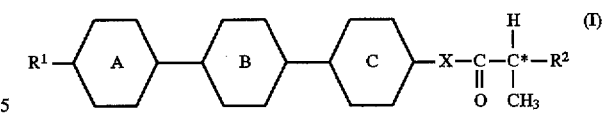

wherein R$^1$ represents a straight-chain or branched alkyl, alkoxy, alkoxycarbonyl, alkanoyloxy or alkoxycarbonyloxy group having 4 to 16 carbon atoms; R$^2$ represents a straight-chain alkyl group having 4 to 10 carbon atoms or a branched alkyl group containing 1 to 3 carbon atoms in its branch and 4 to 12 carbon atoms in total; X represents an oxygen or sulfur atom;

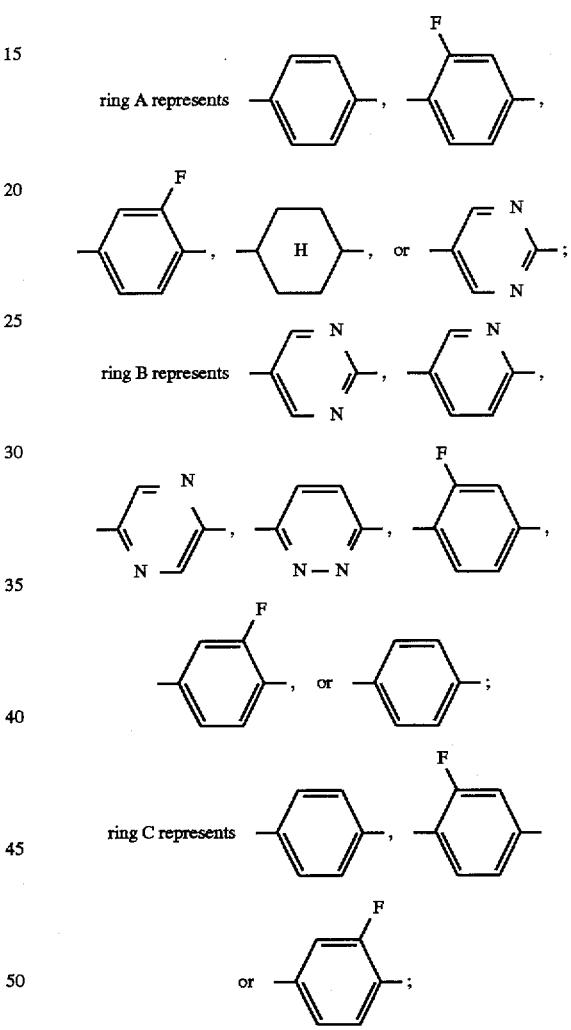

either ring A or ring B represents the above-mentioned nitrogen-containing heterocyclic ring; and C* represents an asymmetric carbon atom.

2. A antiferro-electric liquid crystal composition containing at least one compound represented by formula:

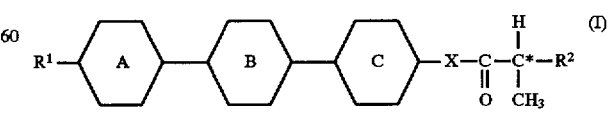

wherein R$^1$ represents a straight-chain or branched alkyl, alkoxy, alkoxycarbonyl, alkanoyloxy or alkoxycarbonyloxy group having 4 to 16 carbon atoms; R$^2$ represents a straight-chain alkyl group having 4 to 10 carbon atoms or a branched alkyl group containing 1 to 3 carbon atoms in its branch and 4 to 12 carbon atoms in total; X represents an oxygen or sulfur atom;

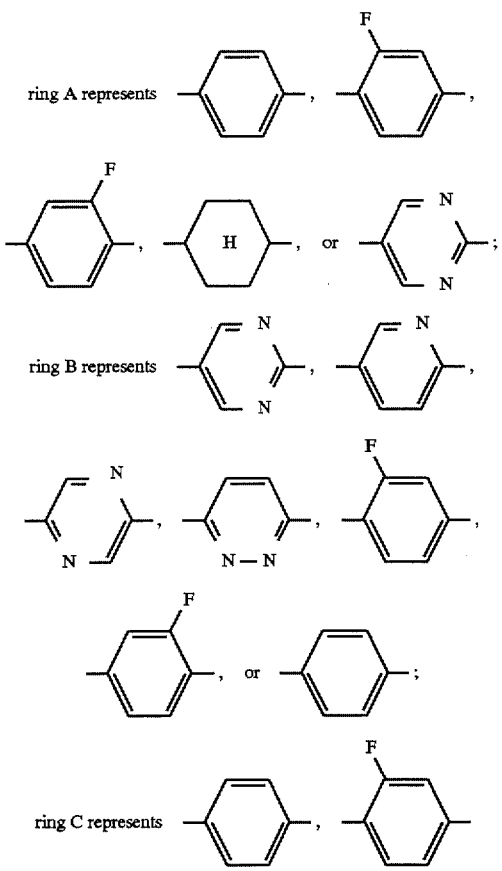

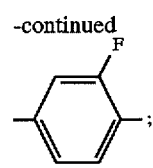

either ring A or ring B represents the above-mentioned nitrogen-containing heterocyclic ring; and C* represents an asymmetric carbon atom.

3. The antiferro-electric liquid crystal compound as claimed in claim 1, wherein the group represented by $R^1$ has 6 to 12 carbon atoms.

4. The antiferro-electric liquid crystal compound as claimed in claim 1, wherein either ring A or B represents a pyrimidine ring.

5. The antiferro-electric liquid crystal composition as claimed in claim 2, wherein the group represented by $R^1$ has 6 to 12 carbon atoms.

6. The antiferro-electric liquid crystal composition as claimed in claim 2, wherein either ring A or B represents a pyrimidine ring.

7. The antiferro-electric liquid crystal composition as claimed in claim 2, further containing an antiferroelectric liquid crystal compound.

8. The antiferro-electric liquid crystal composition as claimed in claim 7, wherein the compound represented by formula (I) is contained in an amount of 1 to 80% by weight.

9. The antiferro-electric liquid crystal composition as claimed in claim 7, wherein the compound represented by formula (I) is contained in an amount of 1 to 40% by weight.

10. The antiferroelectric liquid crystal composition as claimed in claim 2, further containing a compound having a smectic C or chiral smectic C phase in an amount of retaining an antiferroelectric liquid crystal phase of the composition.

* * * * *